US008903489B2

(12) United States Patent
Zhu et al.

(10) Patent No.: US 8,903,489 B2
(45) Date of Patent: *Dec. 2, 2014

(54) METHODS, DEVICES AND SYSTEMS FOR SINGLE-CHAMBER PACING USING A DUAL-CHAMBER PACING DEVICE

(71) Applicant: Cardiac Pacemakers, Inc., St. Paul, MN (US)

(72) Inventors: Qingsheng Zhu, Wexford, PA (US); Daniel Felipe Ortega, Buenos Aires (AR); Julio Cesar Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/650,444

(22) Filed: Oct. 12, 2012

(65) Prior Publication Data

US 2013/0041423 A1    Feb. 14, 2013

Related U.S. Application Data

(63) Continuation of application No. 12/249,508, filed on Oct. 10, 2008, now Pat. No. 8,290,586, which is a (Continued)

(51) Int. Cl.
*A61N 1/362* (2006.01)
*A61N 1/375* (2006.01)

(52) U.S. Cl.
CPC ............. *A61N 1/3627* (2013.01); *A61N 1/3752* (2013.01)
USPC ........................................................... 607/9

(58) Field of Classification Search
None
See application file for complete search history.

(56) References Cited

U.S. PATENT DOCUMENTS 3,614,955 A    10/1971    Mirowski et al.
3,804,098 A     4/1974    Friedman
(Continued)

FOREIGN PATENT DOCUMENTS

DE    2827595 A1    4/1979
DE    3712082 A1    10/1988
(Continued)

OTHER PUBLICATIONS

US 6,875,206, 4/2005, Ponzi (withdrawn).

(Continued)

*Primary Examiner* — Brian T Gedeon
(74) *Attorney, Agent, or Firm* — Schwegman Lundberg & Woessner, P.A.

(57) ABSTRACT

Various embodiments of the present invention are directed to systems, methods and devices for cardiac applications including those relating to pacing devices. One such device is directed to a cardiac rhythm therapy (CRT) device designed for dual chamber pacing using two pacing signals each having a positive and negative component that has been modified for single chamber pacing. The device comprises a first output that connects to a pacing lead; a second output that connects to the pacing lead; a third output that connects to a reference point; and electrical circuitry connecting the second electrical connection to the first output, the third electrical connection to the second output, and the first and fourth electrical connections to the third output.

20 Claims, 9 Drawing Sheets

Related U.S. Application Data continuation-in-part of application No. 12/147,293, filed on Jun. 26, 2008, now Pat. No. 8,014,861, which is a continuation-in-part of application No. 11/300,611, filed on Dec. 13, 2005, now Pat. No. 7,512,440, and a continuation-in-part of application No. 11/300,242, filed on Dec. 13, 2005, now Pat. No. 8,346,358.

(60) Provisional application No. 60/947,308, filed on Jun. 29, 2007, provisional application No. 60/947,310, filed on Jun. 29, 2007, provisional application No. 60/947,322, filed on Jun. 29, 2007, provisional application No. 60/947,327, filed on Jun. 29, 2007, provisional application No. 60/947,336, filed on Jun. 29, 2007, provisional application No. 60/947,342, filed on Jun. 29, 2007, provisional application No. 61/020,511, filed on Jan. 11, 2008.

(56) References Cited

U.S. PATENT DOCUMENTS

| | | | |
|---|---|---|---|
| 3,866,615 | A | 2/1975 | Hewson |
| 3,911,928 | A | 10/1975 | Lagergren |
| 3,942,536 | A | 3/1976 | Mirowski et al. |
| 3,949,757 | A | 4/1976 | Sabel |
| 3,995,623 | A | 12/1976 | Blake et al. |
| 4,026,303 | A | 5/1977 | Babotai |
| 4,030,508 | A | 6/1977 | Thalen |
| 4,057,067 | A | 11/1977 | Lajos |
| 4,106,512 | A | 8/1978 | Bisping |
| 4,136,703 | A | 1/1979 | Wittkampf |
| 4,154,247 | A | 5/1979 | O'Neill |
| 4,217,913 | A | 8/1980 | Dutcher |
| 4,258,725 | A | 3/1981 | O'Neill |
| 4,278,093 | A | 7/1981 | Lafortune et al. |
| 4,282,885 | A | 8/1981 | Bisping |
| 4,289,134 | A | 9/1981 | Bernstein |
| 4,289,144 | A | 9/1981 | Gilman |
| 4,311,153 | A | 1/1982 | Smits |
| 4,332,259 | A | 6/1982 | McCorkle, Jr. |
| 4,365,639 | A | 12/1982 | Goldreyer |
| 4,393,883 | A | 7/1983 | Smyth et al. |
| 4,402,329 | A | 9/1983 | Williams |
| 4,437,474 | A | 3/1984 | Peers-Trevarton |
| 4,458,677 | A | 7/1984 | McCorkle, Jr. |
| 4,458,695 | A | 7/1984 | Peers-Trevarton |
| 4,463,765 | A | 8/1984 | Gold |
| 4,469,104 | A | 9/1984 | Peers-Trevarton |
| 4,497,326 | A | 2/1985 | Curry |
| 4,540,236 | A | 9/1985 | Peers-Trevarton |
| 4,543,956 | A | 10/1985 | Herscovici |
| 4,549,548 | A | 10/1985 | Wittkampf et al. |
| 4,559,951 | A | 12/1985 | Dahl et al. |
| 4,567,901 | A | 2/1986 | Harris |
| 4,570,642 | A | 2/1986 | Kane et al. |
| 4,577,643 | A | 3/1986 | Beranek |
| 4,589,420 | A | 5/1986 | Adams et al. |
| 4,602,645 | A | 7/1986 | Barrington et al. |
| 4,603,705 | A | 8/1986 | Speicher et al. |
| 4,624,265 | A | 11/1986 | Grassi |
| 4,624,266 | A | 11/1986 | Kane |
| 4,627,439 | A | 12/1986 | Harris |
| 4,630,204 | A | 12/1986 | Mortara |
| 4,633,880 | A | 1/1987 | Osypka et al. |
| 4,641,649 | A | 2/1987 | Walinsky et al. |
| 4,643,201 | A | 2/1987 | Stokes |
| 4,646,755 | A | 3/1987 | Kane |
| 4,649,937 | A | 3/1987 | DeHaan et al. |
| 4,649,938 | A | 3/1987 | McArthur |
| 4,662,382 | A | 5/1987 | Sluetz et al. |
| 4,664,113 | A | 5/1987 | Frisbie et al. |
| 4,667,686 | A | 5/1987 | Peers-Travarton |
| H356 | H | 11/1987 | Stokes et al. |
| 4,721,115 | A | 1/1988 | Owens |
| 4,751,931 | A | 6/1988 | Briller et al. |
| 4,784,161 | A | 11/1988 | Skalsky et al. |
| 4,785,815 | A | 11/1988 | Cohen |
| 4,799,486 | A | 1/1989 | DuFault |
| 4,799,493 | A | 1/1989 | DuFault |
| 4,819,647 | A | 4/1989 | Byers et al. |
| 4,819,661 | A | 4/1989 | Heil, Jr. et al. |
| 4,819,662 | A | 4/1989 | Heil, Jr. et al. |
| 4,876,109 | A | 10/1989 | Mayer et al. |
| 4,886,074 | A | 12/1989 | Bisping |
| 4,892,102 | A | 1/1990 | Astrinsky |
| 4,895,152 | A | 1/1990 | Callaghan et al. |
| 4,922,607 | A | 5/1990 | Doan et al. |
| 4,922,927 | A | 5/1990 | Fine et al. |
| 4,924,881 | A | 5/1990 | Brewer |
| 4,953,564 | A | 9/1990 | Berthelsen |
| 4,967,766 | A | 11/1990 | Bradshaw |
| 4,972,848 | A | 11/1990 | DiDomenico et al. |
| 4,987,897 | A | 1/1991 | Funke |
| 4,994,078 | A | 2/1991 | Jarvik |
| 5,002,067 | A | 3/1991 | Berthelsen et al. |
| 5,007,864 | A | 4/1991 | Stutz, Jr. |
| 5,016,646 | A | 5/1991 | Gotthardt et al. |
| 5,036,848 | A | 8/1991 | Hewson |
| 5,050,601 | A | 9/1991 | Kupersmith et al. |
| 5,056,516 | A | 10/1991 | Spehr |
| 5,063,932 | A | 11/1991 | Dahl et al. |
| 5,076,285 | A | 12/1991 | Hess et al. |
| 5,083,564 | A | 1/1992 | Scherlag |
| 5,092,879 | A | 3/1992 | Jarvik |
| 5,129,404 | A | 7/1992 | Spehr et al. |
| 5,144,960 | A | 9/1992 | Mehra et al. |
| 5,152,299 | A | 10/1992 | Soukup |
| 5,174,289 | A | 12/1992 | Cohen |
| 5,179,962 | A | 1/1993 | Dutcher et al. |
| 5,181,511 | A | 1/1993 | Nickolls et al. |
| 5,223,226 | A | 6/1993 | Wittmer et al. |
| 5,242,430 | A | 9/1993 | Arenas et al. |
| 5,255,693 | A | 10/1993 | Dutcher et al. |
| 5,259,394 | A | 11/1993 | Bens |
| 5,259,395 | A | 11/1993 | Li |
| 5,267,560 | A | 12/1993 | Cohen |
| 5,275,620 | A | 1/1994 | Darby et al. |
| 5,282,845 | A | 2/1994 | Bush et al. |
| 5,299,569 | A | 4/1994 | Wernicke et al. |
| 5,300,108 | A | 4/1994 | Rebell et al. |
| 5,304,219 | A | 4/1994 | Chernoff et al. |
| 5,306,292 | A | 4/1994 | Lindegren |
| 5,313,953 | A | 5/1994 | Yomtov et al. |
| 5,320,642 | A | 6/1994 | Scherlag |
| 5,324,327 | A | 6/1994 | Cohen |
| 5,336,252 | A | 8/1994 | Cohen |
| 5,342,414 | A | 8/1994 | Mehra |
| 5,344,439 | A | 9/1994 | Otten |
| 5,358,516 | A | 10/1994 | Myers et al. |
| 5,366,496 | A | 11/1994 | Dahl et al. |
| 5,370,665 | A * | 12/1994 | Hudrlik .................... 607/9 |
| 5,374,286 | A | 12/1994 | Morris |
| 5,381,790 | A | 1/1995 | Kanesaka |
| 5,393,929 | A | 2/1995 | Yagihashi |
| 5,405,373 | A | 4/1995 | Petersson et al. |
| 5,411,544 | A | 5/1995 | Mar et al. |
| 5,425,755 | A | 6/1995 | Doan |
| 5,433,735 | A | 7/1995 | Zanakis et al. |
| 5,439,391 | A | 8/1995 | McEtchin et al. |
| 5,447,533 | A | 9/1995 | Vachon et al. |
| 5,447,534 | A | 9/1995 | Jammet |
| 5,456,706 | A | 10/1995 | Pless et al. |
| 5,456,708 | A | 10/1995 | Doan et al. |
| 5,466,253 | A | 11/1995 | Doan |
| 5,476,497 | A | 12/1995 | Mower et al. |
| 5,476,499 | A | 12/1995 | Hirschberg |
| 5,476,501 | A | 12/1995 | Stewart et al. |
| 5,476,502 | A | 12/1995 | Rubin |
| 5,492,119 | A | 2/1996 | Abrams |
| 5,500,008 | A | 3/1996 | Fain |
| 5,514,172 | A | 5/1996 | Mueller |
| 5,515,848 | A | 5/1996 | Corbett, III et al. |

(56) References Cited

U.S. PATENT DOCUMENTS

| | | |
|---|---|---|
| 5,522,874 A | 6/1996 | Gates |
| 5,524,338 A | 6/1996 | Martyniuk et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,681,013 A | 10/1997 | Peck et al. |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |
| 5,755,766 A | 5/1998 | Chastain et al. |
| 5,769,881 A | 6/1998 | Schroeppel et al. |
| 5,772,693 A | 6/1998 | Brownlee |
| 5,782,898 A | 7/1998 | Dahl et al. |
| 5,800,464 A | 9/1998 | Kieval |
| 5,800,465 A | 9/1998 | Thompson et al. |
| 5,807,306 A | 9/1998 | Shapland et al. |
| 5,810,887 A | 9/1998 | Accorti, Jr. et al. |
| 5,814,077 A | 9/1998 | Sholder et al. |
| 5,814,079 A | 9/1998 | Kieval |
| 5,851,227 A | 12/1998 | Spehr |
| 5,871,506 A | 2/1999 | Mower |
| 5,871,529 A | 2/1999 | Bartig et al. |
| 5,871,531 A | 2/1999 | Struble |
| 5,876,399 A | 3/1999 | Chia et al. |
| 5,876,431 A | 3/1999 | Spehr et al. |
| 5,916,214 A | 6/1999 | Cosio et al. |
| 5,925,045 A | 7/1999 | Reimels et al. |
| 5,935,159 A | 8/1999 | Cross, Jr. et al. |
| 5,941,868 A | 8/1999 | Kaplan |
| 5,944,710 A | 8/1999 | Dev et al. |
| 5,964,795 A | 10/1999 | McVenes et al. |
| 5,972,416 A | 10/1999 | Reimels et al. |
| 5,995,871 A | 11/1999 | Knisley |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,096,069 A | 8/2000 | Bischoff |
| 6,123,084 A | 9/2000 | Jandak et al. |
| 6,141,588 A | 10/2000 | Cox et al. |
| 6,141,594 A | 10/2000 | Flynn et al. |
| 6,144,879 A | 11/2000 | Gray |
| 6,161,029 A | 12/2000 | Spreigl et al. |
| 6,165,164 A | 12/2000 | Hill et al. |
| 6,212,434 B1 | 4/2001 | Scheiner et al. |
| 6,219,581 B1 | 4/2001 | Schaldach et al. |
| 6,230,061 B1 | 5/2001 | Hartung |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,309,370 B1 | 10/2001 | Haim et al. |
| 6,341,235 B1 | 1/2002 | Mower |
| 6,345,204 B1 | 2/2002 | Scheiner et al. |
| 6,358,247 B1 | 3/2002 | Altman et al. |
| 6,363,286 B1 | 3/2002 | Zhu et al. |
| 6,416,510 B1 | 7/2002 | Altman et al. |
| 6,463,334 B1 | 10/2002 | Flynn et al. |
| 6,468,263 B1 | 10/2002 | Fischell et al. |
| 6,471,697 B1 | 10/2002 | Lesh |
| 6,484,057 B2 | 11/2002 | Ideker et al. |
| 6,505,082 B1 | 1/2003 | Scheiner et al. |
| 6,535,766 B1 | 3/2003 | Thompson et al. |
| 6,540,725 B1 | 4/2003 | Ponzi |
| 6,542,775 B2 | 4/2003 | Ding et al. |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,643,546 B2 | 11/2003 | Mathis et al. |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,766,190 B2 | 7/2004 | Ferek-Petric |
| 6,768,923 B2 | 7/2004 | Ding et al. |
| 6,801,807 B2 | 10/2004 | Abrahamson |
| 6,804,555 B2 | 10/2004 | Warkentin |
| 6,810,286 B2 | 10/2004 | Donovan et al. |
| 6,855,124 B1 | 2/2005 | Gonzalez et al. |
| 6,901,289 B2 | 5/2005 | Dahl et al. |
| 6,904,316 B2 | 6/2005 | Kramer |
| 6,905,476 B2 | 6/2005 | Ponzi |
| 6,907,285 B2 | 6/2005 | Denker et al. |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 6,937,897 B2 | 8/2005 | Min et al. |
| 7,027,876 B2 | 4/2006 | Casavant et al. |
| 7,039,462 B2 | 5/2006 | Pastore et al. |
| 7,096,051 B1 | 8/2006 | Alder |
| 7,113,825 B2 | 9/2006 | Pastore et al. |
| 7,130,682 B2 | 10/2006 | Stahmann et al. |
| 7,187,970 B2 | 3/2007 | Shemer et al. |
| 7,245,973 B2 | 7/2007 | Liu et al. |
| 7,257,443 B2 | 8/2007 | Pastore et al. |
| 7,280,872 B1 | 10/2007 | Mosesov et al. |
| 7,317,950 B2 | 1/2008 | Lee |
| 7,319,900 B2 | 1/2008 | Kim et al. |
| 7,359,837 B2 | 4/2008 | Drew |
| 7,392,095 B2 | 6/2008 | Flynn et al. |
| 7,395,042 B2 | 7/2008 | Alder |
| 7,400,931 B2 | 7/2008 | Mandrusov et al. |
| 7,460,914 B2 | 12/2008 | Mandrusov et al. |
| 7,509,170 B2 | 3/2009 | Zhang et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,078,287 B2 | 12/2011 | Liu et al. |
| 8,290,586 B2 | 10/2012 | Zhu et al. |
| 8,346,358 B2 | 1/2013 | Ortega et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0049478 A1 | 4/2002 | Ding et al. |
| 2002/0058981 A1 | 5/2002 | Zhu et al. |
| 2002/0099413 A1 | 7/2002 | Mower |
| 2002/0120318 A1 | 8/2002 | Kroll et al. |
| 2002/0169484 A1 | 11/2002 | Mathis et al. |
| 2002/0183720 A1 | 12/2002 | Hill et al. |

(56) References Cited

U.S. PATENT DOCUMENTS

| | | |
|---|---|---|
| 2002/0193836 A1 | 12/2002 | Schmidt |
| 2002/0198583 A1 | 12/2002 | Rock et al. |
| 2003/0009145 A1 | 1/2003 | Struijker-Boudier et al. |
| 2003/0032938 A1 | 2/2003 | Altman |
| 2003/0069625 A1 | 4/2003 | Ley et al. |
| 2003/0078625 A1 | 4/2003 | Casavant |
| 2003/0083700 A1 | 5/2003 | Hill |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0006265 A1 | 1/2004 | Alhussiny |
| 2004/0064176 A1 | 4/2004 | Min et al. |
| 2004/0098057 A1 | 5/2004 | Pastore |
| 2004/0104782 A1 | 6/2004 | Ruffieux |
| 2004/0106958 A1 | 6/2004 | Mathis et al. |
| 2004/0122484 A1 | 6/2004 | Hatlestad et al. |
| 2004/0153127 A1 | 8/2004 | Gordon et al. |
| 2004/0186546 A1 | 9/2004 | Mandrusov et al. |
| 2004/0193223 A1 | 9/2004 | Kramer et al. |
| 2004/0213770 A1 | 10/2004 | Seward et al. |
| 2004/0214182 A1 | 10/2004 | Sharma et al. |
| 2004/0215240 A1 | 10/2004 | Lovett et al. |
| 2004/0215249 A1 | 10/2004 | Corbucci |
| 2004/0215251 A1 | 10/2004 | Sharma et al. |
| 2004/0260374 A1 | 12/2004 | Zhang et al. |
| 2005/0049516 A1 | 3/2005 | Ideker |
| 2005/0075677 A1 | 4/2005 | Ganion et al. |
| 2005/0102002 A1 | 5/2005 | Salo et al. |
| 2005/0125041 A1 | 6/2005 | Min et al. |
| 2005/0136385 A1 | 6/2005 | Mann |
| 2005/0137671 A1 | 6/2005 | Liu et al. |
| 2005/0152516 A1 | 7/2005 | Wang et al. |
| 2005/0159725 A1 | 7/2005 | Tockman et al. |
| 2005/0203580 A1 | 9/2005 | Prentice et al. |
| 2005/0267557 A1 | 12/2005 | Flynn et al. |
| 2005/0277993 A1 | 12/2005 | Mower |
| 2006/0030810 A1 | 2/2006 | Mandrusov et al. |
| 2006/0064027 A1 | 3/2006 | Borowitz et al. |
| 2006/0104596 A1 | 5/2006 | Askins et al. |
| 2006/0116596 A1 | 6/2006 | Zhou et al. |
| 2006/0136001 A1 | 6/2006 | Ortega et al. |
| 2006/0142812 A1 | 6/2006 | Ortega et al. |
| 2006/0224197 A1 | 10/2006 | Havel et al. |
| 2006/0224224 A1 | 10/2006 | Muhlenberg et al. |
| 2006/0253156 A1 | 11/2006 | Pastore et al. |
| 2007/0027488 A1 | 2/2007 | Kaiser et al. |
| 2007/0060961 A1 | 3/2007 | Echt et al. |
| 2007/0093872 A1 | 4/2007 | Chirife et al. |
| 2007/0093874 A1 | 4/2007 | Chirife et al. |
| 2007/0100380 A1 | 5/2007 | Fukui |
| 2007/0129764 A1 | 6/2007 | Burnes |
| 2007/0208387 A1 | 9/2007 | Mower |
| 2007/0232949 A1 | 10/2007 | Saksena |
| 2007/0233216 A1 | 10/2007 | Liu et al. |
| 2007/0239219 A1 | 10/2007 | Salo et al. |
| 2008/0262587 A1 | 10/2008 | Flynn et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1 | 12/2008 | Zhu et al. |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0093859 A1 | 4/2009 | Ortega et al. |
| 2009/0093861 A1 | 4/2009 | Ortega et al. |
| 2009/0099619 A1 | 4/2009 | Lessmeier et al. |
| 2009/0105778 A1 | 4/2009 | Lee et al. |
| 2009/0259272 A1 | 10/2009 | Reddy et al. |
| 2010/0042176 A1 | 2/2010 | Snell |
| 2010/0318147 A1 | 12/2010 | Forslund et al. |
| 2011/0264158 A1 | 10/2011 | Dong et al. |
| 2011/0307026 A1 | 12/2011 | Zhu et al. |
| 2011/0319956 A1 | 12/2011 | Zhu et al. |
| 2012/0041500 A1 | 2/2012 | Zhu et al. |
| 2012/0041503 A1 | 2/2012 | Zhu et al. |
| 2012/0053651 A1 | 3/2012 | Zhu et al. |
| 2012/0101539 A1 | 4/2012 | Zhu et al. |

FOREIGN PATENT DOCUMENTS

| | | |
|---|---|---|
| EP | 0042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| EP | 2164560 A1 | 2/2010 |
| EP | 2164562 A1 | 3/2010 |
| FR | 2465489 A1 | 3/1981 |
| FR | 2575925 A1 | 7/1986 |
| FR | 2757773 A1 | 7/1998 |
| GB | 2240721 A | 8/1991 |
| JP | 5501211 A | 3/1993 |
| JP | 06312025 A | 11/1994 |
| JP | 10052507 A | 2/1998 |
| JP | 2004351122 A | 12/2004 |
| JP | 2005507720 A | 3/2005 |
| JP | 2008523950 A | 7/2008 |
| JP | 2008539894 A | 11/2008 |
| WO | WO-9220401 A1 | 11/1992 |
| WO | WO-9422525 A1 | 10/1994 |
| WO | WO-9615665 A2 | 5/1996 |
| WO | WO-9740883 A1 | 11/1997 |
| WO | WO-0074773 A1 | 12/2000 |
| WO | WO-03035170 A1 | 5/2003 |
| WO | WO-2005011475 A2 | 2/2005 |
| WO | WO-2006068880 A1 | 6/2006 |
| WO | WO-2006115659 A1 | 11/2006 |
| WO | WO-2008063498 A1 | 5/2008 |
| WO | WO-2009006321 A2 | 1/2009 |
| WO | WO-2009006325 A1 | 1/2009 |
| WO | WO-2009006327 A1 | 1/2009 |
| WO | WO-2009006331 A1 | 1/2009 |
| WO | WO-2009006339 A1 | 1/2009 |
| WO | WO-2009078751 A1 | 6/2009 |
| WO | WO-2010042910 A1 | 4/2010 |
| WO | WO-2010071849 A2 | 6/2010 |
| WO | WO-2011139691 A1 | 11/2011 |

OTHER PUBLICATIONS

"U.S. Appl. No. 10/004,695, Response filed Mar. 9, 2004 to Non-Final Office Action mailed Dec. 22, 2003", 8 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

(56) References Cited

OTHER PUBLICATIONS

"U.S. Appl. No. 10/745,302, Restriction Requirement mailed Aug. 12, 2005", 7 pgs.
"U.S. Appl. No. 11/300,242, Final Office Action mailed Aug. 4, 2009", 9 pgs.
"U.S. Appl. No. 11/300,242, Non Final Office Action mailed May 12, 2011", 9 pgs.
"U.S. Appl. No. 11/300,242, Non-Final Office Action mailed Mar. 27, 2008", 8 pgs.
"U.S. Appl. No. 11/300,242, Notice of Allowance mailed Jan. 24, 2012", 5 pgs.
"U.S. Appl. No. 11/300,242, Notice of Allowance mailed May 8, 2012", 6 pgs.
"U.S. Appl. No. 11/300,242, Response filed Feb. 4, 2010 to Final Office Action mailed Aug. 4, 2009", 11 pgs.
"U.S. Appl. No. 11/300,242, Response filed Apr. 2, 2009 to Restriction Requirement mailed Dec. 15, 2008", 8 pgs.
"U.S. Appl. No. 11/300,242, Response filed Sep. 12, 2011 to Non Final Office Action mailed May 12, 2011", 8 pgs.
"U.S. Appl. No. 11/300,242, Response filed Sep. 26, 2008 to Non-Final Office Action mailed Mar. 27, 2008", 10 pgs.
"U.S. Appl. No. 11/300,242, Restriction Requirement mailed Dec. 15, 2008", 10 pgs.
"U.S. Appl. No. 11/300,611, 312 Amendment filed Feb. 9, 2009", 9 pgs.
"U.S. Appl. No. 11/300,611, Non-Final Office Action mailed Mar. 20, 2008", 7 pgs.
"U.S. Appl. No. 11/300,611, Notice of Allowance mailed Jan. 26, 2009", 7 pgs.
"U.S. Appl. No. 11/300,611, PTO Response to 312 Amendment mailed Feb. 26, 2009", 3 pgs.
"U.S. Appl. No. 11/300,611, Response filed Sep. 22, 2008 to Non-Final Office Action mailed Mar. 20, 2008", 12 pgs.
"U.S. Appl. No. 12/147,293, Notice of Allowance mailed Apr. 8, 2011", 12 pgs.
"U.S. Appl. No. 12/147,293, Response filed Feb. 8, 2011 to Restriction Requirement mailed Oct. 8, 2010", 9 pgs.
"U.S. Appl. No. 12/147,293, Restriction Requirement mailed Oct. 8, 2010", 12 pgs.
"U.S. Appl. No. 12/147,317, Examiner Interview Summary mailed Mar. 15, 2011", 3 pgs.
"U.S. Appl. No. 12/147,317, Final Office Action mailed Oct. 12, 2011", 6 pgs.
"U.S. Appl. No. 12/147,317, Non-Final Office Action mailed Dec. 28, 2010", 7 pgs.
"U.S. Appl. No. 12/147,317, Response filed Apr. 11, 2012 to Final Office Action mailed Oct. 12, 2011", 8 pgs.
"U.S. Appl. No. 12/147,317, Response filed Jul. 27, 2011 to Non Final Office Action mailed Dec. 28, 2010", 11 pgs.
"U.S. Appl. No. 12/147,339, Notice of Allowance mailed Mar. 30, 2011", 9 pgs.
"U.S. Appl. No. 12/147,339, Notice of Allowance mailed Dec. 22, 2010", 8 pgs.
"U.S. Appl. No. 12/147,339, Response filed Oct. 20, 2010 to Restriction Requirement mailed Oct. 8, 2010", 7 pgs.
"U.S. Appl. No. 12/147,339, Restriction Requirement mailed Oct. 8, 2010", 7 pgs.
"U.S. Appl. No. 12/147,356, Notice of Allowance mailed Feb. 10, 2011", 17 pgs.
"U.S. Appl. No. 12/147,356, Notice of Allowance mailed Jun. 30, 2011", 15 pgs.
"U.S. Appl. No. 12/147,356, Response filed Nov. 10, 2010 to Restriction Requirement mailed Oct. 12, 2010", 9 pgs.
"U.S. Appl. No. 12/147,356, Restriction Requirement mailed Oct. 12, 2010", 7 pgs.
"U.S. Appl. No. 12/147,369, Non-Final Office Action mailed Sep. 10, 2010", 10 pgs.
"U.S. Appl. No. 12/147,369, Notice of Allowance mailed Apr. 21, 2011", 7 pgs.
"U.S. Appl. No. 12/147,369, Response filed Feb. 10, 2011 to Non Final Office Action mailed Sep. 10, 2010", 7 pgs.
"U.S. Appl. No. 12/147,376, Final Office Action mailed Apr. 20, 2011", 11 pgs.
"U.S. Appl. No. 12/147,376, Non Final Office Action mailed Oct. 3, 2011", 8 pgs.
"U.S. Appl. No. 12/147,376, Non-Final Office Action mailed Sep. 15, 2010", 9 pgs.
"U.S. Appl. No. 12/147,376, Notice of Allowance mailed Mar. 19, 2012", 7 pgs.
"U.S. Appl. No. 12/147,376, Response filed Feb. 15, 2011 to Non Final Office Action mailed Sep. 15, 2010", 9 pgs.
"U.S. Appl. No. 12/147,376, Response filed Feb. 29, 2012 to Non Final Office Action mailed Oct. 3, 2011", 6 pgs.
"U.S. Appl. No. 12/147,376, Response filed Aug. 22, 2011 to Final Office Action mailed Apr. 20, 2011", 8 pgs.
"U.S. Appl. No. 12/147,425, Non-Final Office Action mailed Sep. 15, 2010", 10 pgs.
"U.S. Appl. No. 12/147,425, Notice of Allowance mailed Apr. 19, 2011", 8 pgs.
"U.S. Appl. No. 12/147,425, Response filed Feb. 15, 2011 to Non Final Office Action mailed Sep. 15, 2010", 8 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Non Final Office Action mailed Apr. 6, 2011", 8 pgs.
"U.S. Appl. No. 12/249,454, Response filed Aug. 30, 2011 to Non Final Office Action mailed Apr. 6, 2011", 14 pgs.
"U.S. Appl. No. 12/249,479, Final Office Action mailed Dec. 2, 2011", 8 pgs.
"U.S. Appl. No. 12/249,479, Non Final Office Action mailed Apr. 5, 2011", 10 pgs.
"U.S. Appl. No. 12/249,479, Response filed Apr. 2, 2012 to Final Office Action mailed Dec. 2, 2011", 9 pgs.
"U.S. Appl. No. 12/249,479, Response filed Aug. 30, 2011 to Non Final Office Action mailed Apr. 5, 2011", 12 pgs.
"U.S. Appl. No. 12/412,808, Final Office Action mailed Nov. 21, 2011", 6 pgs.
"U.S. Appl. No. 12/412,608, Non Final Office Action mailed May 26, 2011", 8 pgs.
"U.S. Appl. No. 12/412,608, Response filed Apr. 18, 2012 to Final Office Action mailed Nov. 21, 2011", 7 pgs.
"U.S. Appl. No. 12/412,608, Response filed Sep. 26, 2011 to Non Final Office Action mailed May 26, 2011", 9 pgs.
"ATROSTIM Phrenic Nerve Stimulator", Product Brochure, AtroTech Oy, P.O. Box 28, FIN-33721 Tampere, Finland, (Jun. 2004), 2 pgs.
"Australian Application Serial No. 2005319498, First Examiner Report mailed May 27, 2010", 3 pgs.
"Australian Application Serial No. 2005319498, Response filed Feb. 21, 2011 to First Examiner Report mailed May 27, 2010", 11 pgs.
"Coating Process for Composite Implants", Medical Materials Update, vol. 1, No. 12, (Jan. 1995), 3 pgs.
"European Application Serial No. 05849548.2, Communication and Supplementary Partial European Search Report mailed Feb. 29, 2008", 8 pgs.
"European Application Serial No. 05849548.2, Communication mailed Jun. 9, 2009", 3 pgs.
"European Application Serial No. 05849548.2, Office Action mailed Dec. 20, 2010", 4 pgs.
"European Application Serial No. 05849548,2, Response filed Jun. 29, 2011 to Non Final Office Action mailed Dec. 20, 2010", 9 pgs.
"European Application Serial No. 05849548.2, Response filed Dec. 16, 2009 to Communication mailed Jun. 9, 2009", 10 pgs.
"European Application Serial No. 08772198.1, Office Action mailed Sep. 13, 2010", 6 pgs.
"European Application Serial No. 08772198.1, Response filed Mar. 31, 2011 to Communication mailed Sep. 30, 2010", 11 pgs.
"European Application Serial No. 08781107.1, Invitation Pursuant to Rule 63(1) EPC mailed Jul. 13, 2010", 3 pgs.

(56) References Cited

OTHER PUBLICATIONS

"European Application Serial No. 08781107.1, Communication dated Feb. 9, 2010", 2 pgs.
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08781107.1, Response filed Jun. 14, 2011 to Communication mailed Dec. 14, 2010", 10 pgs.
"European Application Serial No. 08781107.1, Response filed Sep. 22, 2010 to the Invitation to Rule 63(1)", 11 pgs.
"European Application Serial No. 08796045.6, European Search Report mailed Sep. 21, 2010", 6 pgs.
"European Application Serial No. 08796045.6, Office Action mailed Jan. 4, 2012", 4 pgs.
"European Application Serial No. 08796045.6, Response filed Apr. 15, 2011 to Communication dated Oct. 8, 2010", 10 pgs.
"Implant Attaches to Bone by Chemical Bond", Medical Materials Update, vol. 4, No. 7, (Aug. 1997), 2 pgs.
"International Application Serial No. PCT/US05/45044, International Search Report mailed May 2, 2006", 1 pg.
"International Application Serial No. PCT/US08/68627, International Search Report mailed Sep. 10, 2008", 1 pg.
"International Application Serial No. PCT/US08/68627, Written Opinion mailed Sep. 10, 2008", 4 pgs.
"International Application Serial No. PCT/US08/68632, International Search Report mailed Sep. 11, 2008", 2 pgs.
"International Application Serial No. PCT/US08/68632, Written Opinion mailed Sep. 11, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2005/045044, Written Opinion mailed May 2, 2006", 3 pgs.
"International Application Serial No. PCT/US2008/068618, International Search Report mailed Nov. 26, 2008", 2 pgs.
"International Application Serial No. PCT/US2008/068618, Written Opinion mailed Nov. 26, 2008", 6 pgs.
"International Application Serial No. PCT/US2008/068630, International Search Report mailed Sep. 10, 2008", 1 pg.
"International Application Serial No. PCT/US2008/068630, Written Opinion mailed Sep. 10, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2008/068647, International Search Report mailed Sep. 22, 2008", 2 pgs.
"International Application Serial No. PCT/US2008/068647, Written Opinion mailed Sep. 22, 2008", 4 pgs.
"International Application Serial No. PCT/US2009/060293, International Preliminary Report on Patentability mailed Apr. 12, 2011", 10 pgs.
"International Application Serial No. PCT/US2009/060293, International Search Report mailed Mar. 10, 2010", 6 pgs.
"International Application Serial No. PCT/US2009/060293, Invitation to Pay Additional Fee mailed Dec. 18, 2009", 5 pgs.
"International Application Serial No. PCT/US2009/060293, Written Opinion mailed Mar. 10, 2010", 10 pgs.
"International Application Serial No. PCT/US2009/068859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.

"Japanese Application Serial No. 2007-548289, Final Office Action dated Aug. 2, 2011", (w/ English Translation), 5 pgs.
"Japanese Application Serial No. 2007-548289, Office Action mailed Mar. 6, 2012", (w/ English Translation), 3 pgs.
"Japanese Application Serial No. 2007-548289, Office Action mailed Nov. 24, 2010", (w/ English Translation), 7 pgs.
"Japanese Application Serial No. 2007-548289, Response filed May 20, 2011 to Office Action mailed Nov. 24, 2010", (w/ English Translation of Amended Claims), 9 pgs.
"Japanese Application Serial No. 2007-548289, Response filed Oct. 26, 2011 to Office Action mailed Aug. 3, 2011", (w/ English Translation of Amended Claims), 10 pgs.
"Victrex's Peek Used for Dialysis Machines", Medical Material's Update, vol. 3, No. 3, (Apr. 1996), pp. 1-2.
Alboni, P., "Bundle Branch Blocks Anatomically Located in the His Bundle", Italian Cardiology Journal, 10(12), (w/ English Translation thereof, followed by Italian publication), (1980), 1583-1587.
Al-Khadra, A., et al., "The Role of Electroporation in Defibrillation", Circulation Research, 87(9), (Oct. 2000), 797-804.
Arcot-Krishnamurthy, S., et al., "Timing for His-Bundle Pacing", U.S. Appl. No. 13/277,617, filed Oct. 20, 2011, 40 pgs.
Avitall, B., et al., "Iontophoretic Transmyocardial Drug Delivery. A Novel Approach to Antiarrhythmic Drug Therapy", Circulation, 85(4), (1992), 1582-1593.
Barba-Pichardo, Rafael, et al., "Permanent His-Bundle Pacing in Patients With Infra-Hisian Atrioventricular Block", Rev Esp Cardiol. 59(6), (Mar. 9, 2006), 553-558.
Barton, A. J., et al., "Bacterial Adhesion to Orthopedic Implant Polymers", J. Biomed. Mat. Res., 3(3), (Mar. 1996), 403-410.
Bonanno, C., et al., "Effect on QRS Duration and Feasibility of Septal and Multisite Right Ventricular Pacing", Cardiostimolazione, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously". PACE, 20[Pt. 1], (Apr. 1997), 909-915.
Cantu, F. et al., "Validation of Criteria for Selective His Bundle and Para-Hisian Permanent Pacing", PACE, vol. 29, (Dec. 2006), 1326-1333.
Cantu, Francesco, et al., "A Methodical Approach to Validate Selective His Bundle and para-Hisian Permanent Pacing", [abstract] Oasis, (2006), 1 pg.
Catanzariti, Domenico, et al., "Permanent His Bundle Pacing Does Not Induce Ventricular Dyssynchrony. An Echocardiographic Intrapatient Study of Comparison with Conventional Pacing", [abstract] Oasis, (2006), 1 pg.
Chiu, L., et al., "Method for One-Click Deployment and or Configuration of Real-Time Software System Modifications", U.S. Appl. No. 60/558,921, filed Apr. 2, 2004, 8 pgs.
Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] Europace Supplements, vol. 7, (May 2005), 1 pg.
Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.
Deshiviukh, Praiviod M., et al., "Direct His-Bundle Pacing: Present and Future", PACE, vol. 27, Part II, (Jun. 2004), 862-870.
Dong, Y., et al., "His-Bundle Capture Verification and Monitoring", U.S. Appl. No. 61/328,248, filed Apr. 27, 2010, 40 pgs.
El-Sherif, N., et al., "Normalization of Bundle Branch Block Patterns by Distal His Bundle Pacing: Clinical and Experimental Evidence of Longitudinal Dissociation in the Pathologic His Bundle", Circulation, 57(3), (Mar. 1978), 473-483.
Flynn, David M, et al., "Extendable and Retractable Lead Having a Snap-Fit Terminal Connector", U.S. Appl. No. 11/173,664, filed Jul. 1, 2005, 53 pgs.
Furman, S., et al., "Chapter 5—Permanent Pacemaker Implementation", A Practice of Cardiac Pacing, Futura Publishing Co., Inc. Mount Kisco, NY, (1986), 97-127.
Genc, S., et al., "Methodology for Locking Feature Selection in Integral Snap-Fit Assembly", Proceedings of DETC '97, 1997 ASME Engineering Technical Conferences, (Sep. 1997), 1-11.

(56) References Cited

OTHER PUBLICATIONS

Golia, P., et al., "Multisite Pacing of Right Ventricle in Heart Failure: Echocardiographic Evaluation", [Abstract] Cardiostimolazione, vol. 14, No. 3, (Sep. 1996), 5 pgs.

Grosfeld, M. J.W., et al., "Testing a New Mechanism for Left Interventricular Septal Pacing: The Transseptal Route", Europace, vol. 4, (Oct. 2002), 439-444.

Ha, S. W., et al., "Plasma-Sprayed Hydroxylapatite Coating on Carbon Fibre Reinforced Thermoplastic Composite Materials", J. Mater. Sci. Mater. Med., vol. 5, No. 6-7, (1994), pp. 481-484.

Hummel, J. D., et al., "Augmentation of Cardiac Output by Anodal Pacing", [Abstract] Circulation, 90(No. 4, Part 2), (Oct. 1994), p. I-69.

Ingle, Frank, et al., "Lead Motion Sensing via Cable Mcrophonics", U.S. Appl. No. 61/359,430, filed Jun. 29, 2010, 52 pgs.

Jockisch, K. A., et al., "Biological Response to Chopped-Carbon-Fiber-Reinforced Peek", J. Biomed. Mater. Res., vol. 26, No. 2, (1992), pp. 133-146.

Kanno, S., et al., "Establishment of a simple and practical procedure applicable to therapeutic angiogenesis", Circulation, 99(20), (May 25, 1999), 2682-2687.

Kavanagh, K. M., et al., "Monophasic Versus Biphasic Cardiac Stimulation: Mechanism of Decreased Energy Requirements", PACE, vol. 13, No. 10, (Oct. 1990), 10 pgs.

Kaye, D. M., et al., "Frequency-dependent activation of a constitutive nitric oxide synthase and regulation of contractile function in adult rat ventricular myocytes", Circulation Research, 78(2), (Feb. 1996), 217-24.

Knapp, C. P, et al., "Snap Fit Terminal Connector", U.S. Appl. No. 09/184,226, filed Nov. 2, 1998, 39 pgs.

Kutarski, A., et al., "Factors Influencing Differences of RVA & RVOT Pacing Hemodynamic Effects", [abstract CP05] Europace Supplements, vol. 7, (May 2005), p. 288.

Kutarski, A., et al., "Right Ventricular Outflow Tract and Dual Site Right Ventricular Pacing—The Comparison With Apex Pacing", [abstract CP08] Europace Supplements, vol. 7, (May 2005), p. 288.

Labhasetwar, V., et al., "Iontophoresis for Modulation of Cardiac Drug Delivery in Dogs", Proc. Natl. Acad.Sci, USA, 92(7), (Mar. 28, 1995), 2612-2616.

Lazarus, A., et al., "Reduction in Energy Pacing Thresholds by Overlapping Biphasic Stimulation Versus Conventional Bipolar Pacing", PACE, vol. 21, (Nov. 1998), 6 pgs.

Lin, T. W., et al., "Glass Peek Composite Promotes Proliferation and Osteocalcin of Human Osteoblastic Cells", J. Biomed. Mater. Res., vol. 36, No. 2, (1997), pp. 137-144.

Lupi. G., et al., "Effects of Right Ventricular Pacing on Intra-Left Ventricular Electromechanical Activation in Patients with Native Narrow QRS.", American Journal of Cardiology. vol. 98, (2006), 219-222.

Macnair, R., et al., "The Response of Primary Rat and Human Osteoblasts and an Immortalized Rat Osteoblast Cell Line to Orthopaedic Materials: Comparative Sensitivity of Several Toxicity Indices", J. Mater. Sci. Mater. Med., vol. 8, No. 2, (1997), pp. 105-111.

Manolis, Antonis S., "The Deleterious Consequences of Right Ventricular Apical Pacing: Time to Seek Alternate Site Pacing", PACE, vol. 29, (Mar. 2006), 298-315.

Mansourati, J., et al,, "Left ventricular-based pacing in patients with chronic heart failure: comparison of acute hemodynamic benefits according to underlying heart disease", Eur J Heart Fail., 2(2): (Jun. 2000), 195-9.

Meyer, M. R., et al., "Long-Term Durability of the Interface in FRP Composites After Exposure to Simulated Physiologic Saline Environments", J. Biomed. Mater. Res., 28(10), (1994), 1221-1231.

Mond, Harry G. et al., "The Right Ventricular Outflow Tract: The Road to Septal Pacing", PACE, vol. 30, (Apr. 2007), 482-491.

Morina-Vazquez, Pablo, et al., "Cardiac Resynchronization Through Selective His Bundle Pacing in a Patient with the So-Called InfraHis Atrioventricular Block", PACE, vol. 28, (Jul. 2005), 726-729.

Morrison, C., et al., "In Vitro Biocompatibility Testing of Polymers for Orthopaedic Implants Using Cultured Fibroblasts and Osteoblasts", Biomaterials, vol. 16, No. 13, (1995), 987-992.

Narula, O. S, "Longitudinal dissociation in the His bundle. Bundle branch block due to asynchronous conduction within the His bundle in man", Circulation, 56(6), (Dec. 1977), 996-1006.

Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the American College of Cardiology, 47(10), (May 16, 2006), 1938-1945.

Padeletti, Luigi, et al., "Physiologic Pacing: New Modalities and Pacing Sites", PACE, vol. 29, Supplement 2, (Dec. 2006), S73-S77.

Pastore, G., et al., "Different Degree of Ventricular Dyssyncrony Induced by Right Apical, Hissian and Para Hissian Ventricular Pacing", [abstract] Oasis, (2006), 1 pg.

Pastore, Gianni, et al., "Direct His-Bundle Pacing Preserves the Normal Left Activation Sequence: An Acute Echocardiographic Study", [abstract] Oasis, (2006), 1 pg.

Puech, P., et al., "Narrowing and normalization of QRS stimulation of the His bundle in complete left bundle branch block.", Scholarly Journal of the French Cardiology Society, vol. 72, No. 8, (w/ English Translation thereof, followed by French publication), (Aug. 1979), 815-824.

Qu, J, et al., "HCN2 overexpression in newborn and adult ventricular myocytes: distinct effects on gating and excitability", Circ, Res., vol. 89(1), (Jul. 6, 2001), e8-14.

Qu, J, et al., "Sympathetic innervation alters activations of pacemaker current (If) in rat ventricle", J. Physiol, 526 Pt 3, (Aug. 1, 2000), 561-569.

Ravazzi, A., et al., "Improvement of Interventricular Activation Time Using Biphasic Pacing Pulses at Different Sites on Right Ventricle Septal Wall", Progress in Biomedical Research, 4(3). (Jun. 1999), 248-253.

Reddy, G. S., "Bundle of His Stimulation System", U.S. Appl. No, 61/045,168, filed Apr. 15, 2008, 37 pgs.

Saksena, S., et al., "Chapter 9—Pacemaker Implantation Techniques", Electrical Therapy for Cardiac Arrhythmias, W.B. Saunders Co., Philadelphia, PA, (1990), pp. 173, 183-183.

Scheinman, M. M., et al., "Long-Term His-Bundle Pacing and Cardiac Function", Circulation, 101(8), (2000), 836-837.

Schoenfeld, M. H., "Alternative Site Pacing to Promote Cardiac Synchrony: Has Conventional Pacing Become Unconventional?", Journal of the American College of Cardiology, 47(10), (2006), 1946-1948.

Shi, W, et al., "Distribution and prevalence of hyperpolarization-activated cation channel (HCN) mRNA expression in cardiac tissues", Circ. Res., vol. 85(1), (Jul. 9, 1999), e1-6.

Sotobata, I., et al,, "Population distribution of Frank-vectorcardiographic measurements of healthy Japanese men", Japanese Circulation Journal, 39(8), (1975), 895-903.

Soyer, J., et al., "Experimental Characterisation of a Carbon/PEEK Hip Prothesis in Fatigue", Chirurgie, 121, (1996), p. 658-663.

Sweeney, M. O., et al., "Adverse Effect of Ventricular Pacing on Heart Failure and Atrial Fibrillation Among Patients with Normal Baseline QRS Duration in a Clinical Trial of Pacemaker Therapy for Sinus Node Dysfunction", Circulation, 107(23), (2003), 2932-2937.

Sweeney, M. O., et al,, "Heart Failure During Cardiac Pacing", Circulation, 113(17), (2006), 2082-2088.

Takatsuki, et al., "Clinical Implications of "pure" Hisian pacing in addition to para-Hisian pacing for the diagnosis of supraventricular tachycardia", Heart Rhythm 3 (12), (Dec. 8, 2006), 1412-1418.

Tanabe, M., et al., "Biventricular Pacing Worsened Dyssynchrony in Heart Failure Patient with Right-Bundle Branch Block", International Journal of Cardiology, 138(3), (available online Aug. 15, 2008 / epub doi:10.1016/j.ijcard.2008.06.063 ), (2010), e47-e50.

Thakral, A, et al., "Effects of anodal vs. cathodal pacing on the mechanical performance of the isolated rabbit heart", J. Appl Physiol., 89(3), (Sep. 2000), 1159-64.

Tse, Hung-Fat, et al., "Selection of Permanent Ventricular Pacing Site: How Far Should We Go?", Journal of the American College of Cardiology, 48(8), (Sep. 26, 2006), 1649-1651.

(56) References Cited

OTHER PUBLICATIONS

Van Gelder, B. M., et al., "Hemodynamic Effect of RV Apex vs RV Septum Pacing in a Monoventricular and Biventricular Configuration in Patients with Heart Failure", [abstract CP06] Europace Supplements, vol. 7, (May 2005), p. 288.

Victor, F., et al., "A Randomized Comparison of Permanent Septal Versus Apical Right Ventricular Pacing: Short-Term Results", Journal of Cardiovascular Electrophysiology, 17(3), (Mar. 2006), 238-242.

Wang, S. C.-J., et al., "Improved Method and System for Managing Voice Prompt Recordings prior to deployment", U.S. Appl. No. 60/532,271, filed Dec. 23, 2003, 12 pgs.

Wenz, L. M,, et al., "In Vitro Biocompatibility of Polyetheretherketone and Polysulfone Composites", J. Biomed, Mater. Res., vol. 26, No. 2, (1990), pp. 207-215.

Winckels, S. K. G., et al., "High-Septal Pacing Reduces Ventricular Electrical Remodeling and Proarrhythmia in Chronic Atrioventricular Block Dogs", Journal of the American College of Cardiology, 50(9), (Aug. 28, 2007), 906-913.

Yu. H., et al., "MinK-related peptide 1: A beta subunit for the HCN ion channel subunit family enhances expression and speeds activation", Cir. Res., 88(12), (Jun. 22, 2001), e84-7.

Zanon, F., et al., "A Feasible Approach for Direct His-Bundle Pacing Using a New Steerable Catheter to Facilitate Precise Lead Placement", Journal of Cardiovascular Electrophysiology, 17(1), (Jan. 2006), 29-33.

Zanon, Francesco, et al., "A New Technique for Direct His-Bundle Pacing: Acute and Mid-Term Electrical Data Results", [abstract] Oasis, (2006), 1 pg.

Zanon, Francesco, et al., "Direct His Bundle Pacing Preserves Coronary Perfusion Compared With Right Ventricular Apical Pacing: A Prospective, Cross-Over Mid-Term Study", Europace, vol. 10, (2008), 580-587.

Zhang, Y., et al., "His Electrogram Alternans Reveal Dual-Wavefront Inputs Into and Longitudinal Dissociation Within the Bundle of His", Circulation,104(7), (2001), 832-838.

Zhu, Q., et al., "Methods, Devices and Systems for Cardiac Pacing Therapies Using Intrinsic Activity", U.S. Appl. No. 61/139,117, filed Dec. 19, 2008, 22 pgs.

"U.S. Appl. No. 11/300,242, Notice of Allowance mailed Aug. 24, 2012", 7 pgs.

"U.S. Appl. No. 12/147,317, Notice of Allowance mailed Jul. 2, 2012", 7 pgs.

"U.S. Appl. No. 12/147,376, Notice of Allowance mailed Aug. 30, 2012", 7 pgs.

"U.S. Appl. No. 12/147,376, Notice of Allowance mailed Dec. 7, 2012", 7 pgs.

"U.S. Appl. No. 12/249,454, Non Final Office Action mailed Sep. 4, 2012", 8 pgs.

"U.S. Appl. No. 12/249,454, Notice of Allowance mailed Dec. 26, 2012", 5 pgs.

"U.S. Appl. No. 12/249,454, Response filed Apr. 2, 2012 to Final Office Action mailed Nov. 23, 2011", 12 pgs.

"U.S. Appl. No. 12/249,454, Response filed Dec. 4, 2012 to Non Final Office Action mailed Sep. 4, 2012", 12 pgs.

"U.S. Appl. No. 12/249,479, Non Final Office Action mailed Sep. 4, 2012", 7 pgs.

"U.S. Appl. No. 12/249,479, Notice of Allowance mailed Jan. 8, 2013", 5 pgs.

"U.S. Appl. No. 12/249,479, Response filed Dec. 4, 2012 to Non Final Office Action mailed Sep. 4, 2012", 9 pgs.

"U.S. Appl. No. 12/249,508, Notice of Allowance mailed Feb. 14, 2012", 7 pgs.

"U.S. Appl. No. 12/249,508, Notice of Allowance mailed Jun. 12, 2012", 7 pgs.

"U.S. Appl. No. 12/249,508, Notice of Allowance mailed Oct. 5, 2011", 9 pgs.

"U.S. Appl. No. 12/412,608, Notice of Allowance mailed Jun. 6, 2012", 7 pgs.

"U.S. Appl. No. 13/211,937, Non Final Office Action mailed Jan. 15, 2013", 7 pgs.

"U.S. Appl. No. 13/211,937, Notice of Allowance mailed May 13, 2013", 6 pgs.

"U.S. Appl. No. 13/211,937, PTO Response to 312 Amendment mailed Aug. 20, 2013", 2 pgs.

"U.S. Appl. No. 13/211,937, Response filed Apr. 11, 2013 to Non Final Office Action mailed Jan. 15, 2013", 8 pgs.

"U.S. Appl. No. 13/216,969, Final Office Action mailed Apr. 7, 2014", 6 pgs.

"U.S. Appl. No. 13/216,969, Non Final Office Action mailed Dec. 18, 2013", 12 pgs.

"U.S. Appl. No. 13/216,969, Response filed Mar. 17, 2014 to Non Final Office Action mailed Dec. 18, 2013", 9 pgs.

"U.S. Appl. No. 13/216,969, Response filed Jun. 9, 2014 to Final Office Action mailed Apr. 7, 2014", 7 pgs.

"U.S. Appl. No. 13/217,776, Non Final Office Action mailed Jan. 15, 2013", 6 pgs.

"U.S. Appl. No. 13/217,776, Notice of Allowance mailed May 15, 2013", 6 pgs.

"U.S. Appl. No. 13/217,776, Response filed Apr. 11, 2013 to Non Final Office Action mailed Jan. 15, 2013", 9 pgs.

"U.S. Appl. No. 13/223,919, Final Office Action mailed Apr. 2, 2014", 6 pgs.

"U.S. Appl. No. 13/223,919, Non Final Office Action mailed Oct. 29, 2013", 11 pgs.

"U.S. Appl. No. 13/223,919, Notice of Allowance mailed Apr. 30, 2014", 5 pgs.

"U.S. Appl. No. 13/223,919, Response filed Feb. 27, 2014 to Non Final Office Action mailed Oct. 29, 2013", 15 pgs.

"U.S. Appl. No. 13/223,919, Response filed Apr. 21, 2014 to Final Office Action mailed Apr. 2, 2014", 8 pgs.

"U.S. Appl. No. 13/282,163 , Response filed Feb. 27, 2014 to Non Final Office Action mailed Oct. 28, 2013", 11 pgs.

"U.S. Appl. No. 13/282,163, Non Final Office Action mailed Oct. 28, 2013", 12 pgs.

"U.S. Appl. No. 13/282,163, Notice of Allowance mailed Apr. 8, 2014", 5 pgs.

"U.S. Appl. No. 13/645,464, Final Office Action mailed Apr. 2, 2014", 6 pgs.

"U.S. Appl. No. 13/645,464, Non Final Office Action mailed Oct. 28, 2013", 10 pgs.

"U.S. Appl. No. 13/645,464, Notice of Allowance mailed Apr. 30, 2014", 5 pgs.

"U.S. Appl. No. 13/645,464, Response filed Feb. 27, 2014 to Non Final Office Action mailed Oct. 28, 2013", 23 pgs.

"U.S. Appl. No. 13/645,464, Response filed Apr. 22, 2014 to Final Office Action mailed Apr. 2, 2014", 8 pgs.

"U.S. Appl. No. 13/688,859, Final Office Action mailed Oct. 8, 2013", 5 pgs.

"U.S. Appl. No. 13/688,859, Non Final Office Action mailed Jun. 20, 2013", 6 pgs.

"U.S. Appl. No. 13/688,859, Notice of Allowance mailed Jan. 27, 2014", 6 pgs.

"U.S. Appl. No. 13/688,859, Response filed Jan. 8, 2014 to Final Office Action mailed Oct. 8, 2013", 7 pgs.

"U.S. Appl. No. 13/688,859, Response filed Sep. 20, 2013 to Non Final Office Action mailed Jun. 20, 2013", 12 pgs.

"U.S. Appl. No. 13/862,776, Non Final Office Action mailed Jun. 2, 2014", 10 pgs.

"U.S. Appl. No. 13/875,681, Non Final Office Action mailed Oct. 17, 2013", 5 pgs.

"U.S. Appl. No. 13/875,681, Notice of Allowance mailed Mar. 28, 2014", 8 pgs.

"U.S. Appl. No. 13/875,681, Response filed Jan. 16, 2014 to Non Final Office Action mailed Oct. 17, 2013", 9 pgs.

"U.S. Appl. No. 14/027,568, Non Final Office Action mailed May 2, 2014", 7 pgs.

"Australian Application Serial No. 2009303324, First Examiner Report mailed May 15, 2013", 4 pgs.

"Australian Application Serial No. 2009303324, Response filed Apr. 8, 2014 to First Examiner Report mailed May 15, 2013", 15 pgs.

(56) References Cited

OTHER PUBLICATIONS

"European Application Serial No. 05849548.2, Office Action mailed Jan. 16, 2013", 3 pgs.

"European Application Serial No. 08772198.1, Examination Notification Art. 94(3) mailed Nov. 27, 2013", 3 pgs.

"European Application Serial No. 08796045.6, Response filed May 14, 2012 to Office Action mailed Jan. 4, 2012", 8 pgs.

"Japanese Application No. 2010-515189, Response Apr. 19, 2013 to Non Final Office Action dated Feb. 12, 2013", With English Claims, 7 pgs.

"Japanese Application No. 2010-515198, Non Final Office Action dated Jul. 2, 2013", With English Translation, 14.

"Japanese Application Serial No. 2007-548289, Office Action mailed Nov. 6, 2012", With English Translation, 3 pgs.

Japanese Application Serial No. 2007-548289, Response filed Feb. 4, 2013 to Office Action mailed Nov. 6, 2012, With English Claims, 7 pgs.

"Japanese Application Serial No. 2007-548289, Response filed Jun. 4, 2012 to Office Action mailed Mar. 6, 2012", With English Translation, 4 pgs.

"Japanese Application Serial No. 2010-515189, Non-Final Office Action dated Jul. 2, 2013", With English Translation, 6.

"Japanese Application Serial No. 2010-515189, Office Action mailed Feb. 12, 2013", With English Translation, 9 pgs.

"Japanese Application Serial No. 2010-515196, Office Action mailed Jan. 15, 2013", With English Translation, 8 pgs.

"Japanese Application Serial No. 2010-515196, Office Action mailed Sep. 3, 2013", With English Translation, 10 pgs.

"Japanese Application Serial No. 2010-515198, Examiners Decision of Final Refusal mailed Nov. 26, 2013", With English Translation, 5 pgs.

"Japanese Application Serial No. 2010-515198, Office Action mailed Feb. 12, 2013", With English Translation, 16 pgs.

"Japanese Application Serial No. 2010-515198, Response filed Apr. 24, 2013 to Office Action mailed Feb. 12, 2013", With English Claims, 7 pgs.

"Japanese Application Serial No. 2011-531237, Office Action mailed Jan. 15, 2013", With English Translation, 7 pgs.

"Japanese Application Serial No. 2011-531237, Office Action mailed Feb. 12, 2012", With English Translation, 6 pgs.

* cited by examiner

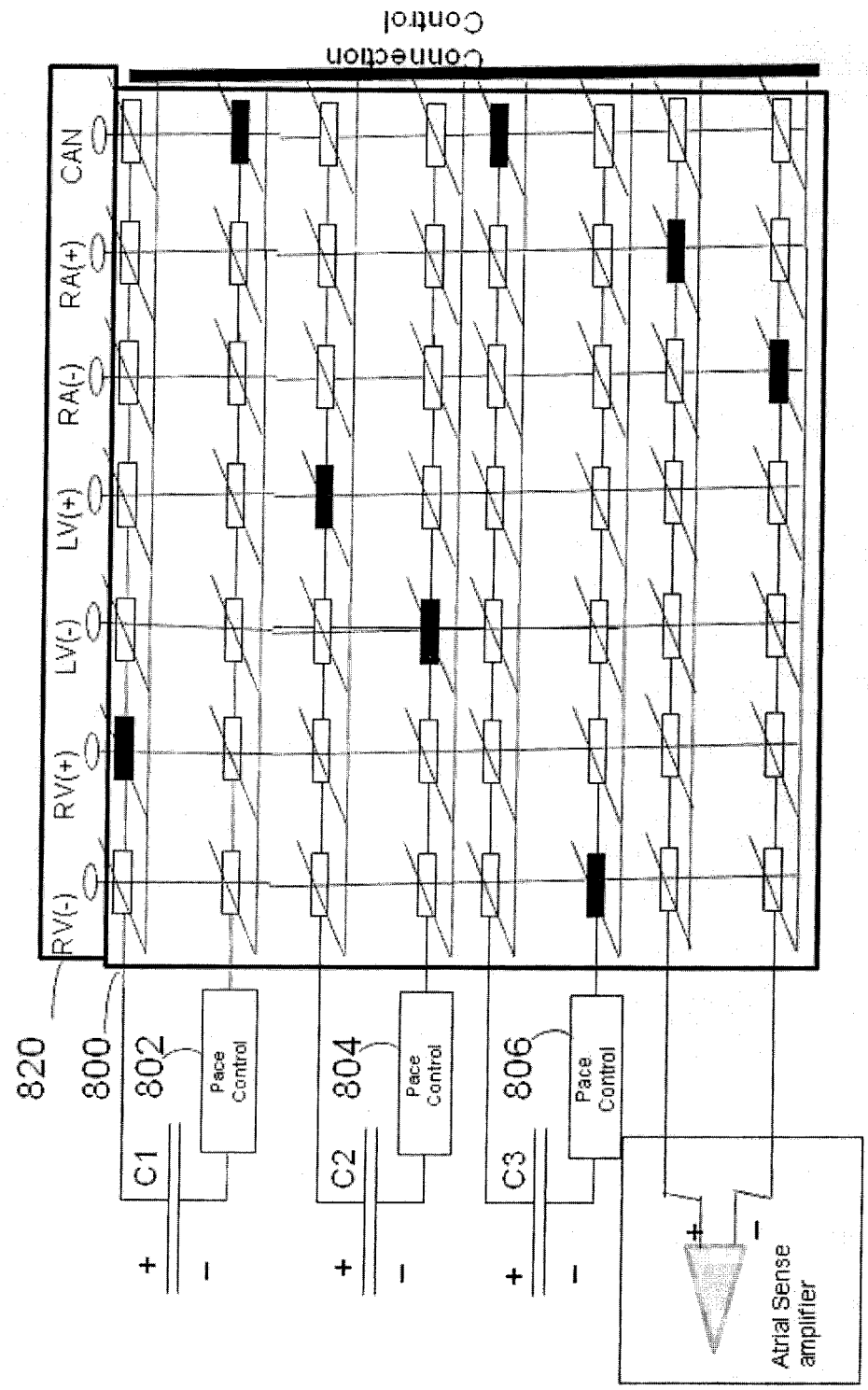

METHODS, DEVICES AND SYSTEMS FOR SINGLE-CHAMBER PACING USING A DUAL-CHAMBER PACING DEVICE

CLAIM OR PRIORITY

This patent document is a continuation of and claims priority under U.S.C. §120 to U.S. patent application Ser. No. 12/249,508 to Qingsheng Zhu et al., and filed Oct. 10, 2008, now issued as U.S. Pat. No. 8,290,586, which is a continuation-in-part of and claims priority under 35 U.S.C. §120 to U.S. patent application Ser. No. 12/147,293 to Qingsheng Zhu et al., and filed Jun. 26, 2008, now issued as U.S. Pat. No. 8,014,861, which in turn claims the benefit, under 35 U.S.C. §119(e), of U.S. Provisional patent applications concurrently filed on Jun. 29, 2007, to Qingsheng Zhu and identified by the following Ser. No. 60/947,308 (Endocardial Pacing For Resynchronization), 60/947,310 (Directable Sheath Arrangement For Ventricular Resynchronization), 60/947,322 (System And Method For Ventricular Pacing With Monitoring And Responsiveness To Pacing Effectiveness), 60/947,327 (Electrical Circuit Arrangement And Method For Pulse Control Of Endocardial Pacing For Resynchronization), 60/947,336 (Endocardial Pacing For Resynchronization And Defibrillator), 60/947,342 (Endocardial Pacing For Resynchronization And Treatment Of Conduction Abnormalities), and of U.S. Provisional Patent Application identified by Ser. No. 61/020,511 (A Cardiac Stimulation Catheter With Two Contacting Electrodes To The Cardiac Tissue And Its Connections To The Stimulator) filed on Jan. 11, 2008 to Qingsheng Zhu et al. and also claims priority under 35 U.S.C. §120 to, as a continuation-in-part of, both U.S. patent application Ser. No. 11/300,611 (Ventricular Pacing) filed Dec. 13, 2005, to Daniel Felipe Ortega et al., now issued as U.S. Pat. No. 7,512,440, and to U.S. patent application Ser. No. 11/300,242 (Pacemaker Which Reestablishes Or Keeps The Physiological Electric Conduction Of The Heart And A Method Of Application) filed Dec. 13, 2005 to Daniel Felipe Ortega et al., now issued as U.S. Pat. No. 8,346,358, which in turn claim priority to Argentine Patent Application Ser. No. 20040104782 (A New Pacemaker Which Reestablishes Or Keeps The Physiological Electric Conduction Of The Heart And A4 Method Of Application) filed Dec. 20, 2004, to Daniel Felipe Ortega et al. Each of these patents documents is incorporated by reference in their entirety.

FIELD OF THE INVENTION

This invention generally relates to systems, devices and methods relating to cardiac monitoring and treatments such as ventricular pacing. More particular aspects of this invention concern use of a cardiac-rhythm therapy arrangement for improving heart function by pacing of a patient's left and right ventricles by providing pacing signals to one or more electrodes residing in the patient's right ventricle.

BACKGROUND

Pacemakers are perhaps the most well known devices that provide chronic electrical stimulus, such as cardiac rhythm management. Modern pacemakers are designed to be implanted within a patient receiving the medical therapy. Other examples of cardiac stimulators include implantable cardiac defibrillators (ICDs) and implantable devices capable of performing pacing and defibrillating functions. Such implantable devices provide electrical stimulation to selected portions of the heart in order to treat disorders of cardiac rhythm. An implantable pacemaker paces the heart with timed pacing pulses. The pacing pulses can be timed relative to other pacing pulses or to sensed (intrinsic) electrical activity. If functioning properly, the pacemaker enforces a minimum heart rate to make up for the heart's inability to pace itself at an appropriate rhythm for metabolic demand. Some pacing devices synchronize pacing pulses delivered to different areas of the heart in order to coordinate the contractions. Coordinated contractions allow the heart to pump efficiently to provide sufficient cardiac output. Clinical data has shown that cardiac resynchronization, achieved through synchronized biventricular pacing, results in a significant improvement in cardiac function. Cardiac resynchronization therapy improves cardiac function in heart failure patients. Heart failure patients have reduced autonomic balance, which is associated with LV (left-ventricular) dysfunction and increased mortality.

Commonly treated conditions relate to the heart beating too fast or too slow. When the heart beats too slow, often leading to a condition referred to as bradycardia, pacing can be used to increase the intrinsic heart rate and correct the condition. When the heart beats too fast, often due to a condition referred to as tachycardia, intrinsic electrical stimulus of the heart itself, in the presence of certain myocardial substrate modifications (i.e., infracted or non-conducting areas), can find a circuit that allows them to re-enter into the original activation circuit and re-trigger a new activation. These re-entrant circuits can lead to very fast heart rates that are undesirable and even fatal. To correct for this condition, antitachycardia pacing at rates higher than the tachyarrhythmia rates can be used to regain control of the heart rhythm by using specialized sequences of pulses and trains of pulses. Once the system delivering the antytachycardia fast pacing takes control of the heart it gradually reduces its pacing rate in the hopes that the normal sinus rhythm will take control again, and reduce the intrinsic heart rate. Antytachycardia pacing is generally used in combination with an implantable defibrillator, because the pacing burst could accelerate the arrhythmia into ventricular fibrillation.

When pacing for bradycardia, percutaneously placed pacing electrodes are commonly positioned in the right-side chambers (right atrium or right ventricle) of the heart. Access to such chambers is readily available through the superior vena cavity, the right atrium, the tricuspid valve and then into the right ventricle. Pacing of both the right atrium and right ventricle was developed. Such dual chamber pacing resulted in better hemodynamic output than right ventricle-only pacing. In addition to treating bradycardia, dual chamber pacing maintained synchrony between the chambers.

Electrode placement in the left ventricle is normally avoided, where access is not as direct as in right ventricle placement. Moreover, emboli risk in the left ventricle is greater than in the right ventricle. Emboli which might develop in the left ventricle by reason of the electrode placement have direct access to the brain via the ascending aorta from the left ventricle. This presents a significant risk of stroke.

Recent clinical evidence suggests that conventional ventricular pacing from the right ventricle creates asynchronous contraction of the left and right ventricles, thereby resulting in inefficient mechanical contraction and reduced hemodynamic performance. Long term right ventricular pacing has even been found to be associated with an increased risk of developing and/or worsening heart failure.

SUMMARY

The present invention is directed to devices and methods for overcoming the above-mentioned challenges and others.

The present invention is exemplified in a variety of implementations and applications, many of which involve tools and methods helpful, or particularly suited, for certain cardiac conditions advantaged by ventricular pacing. Aspects of the present invention are exemplified by ventricular pacing of the right and left ventricles from a lead in the right ventricle. Embodiments may be used, among other applications, to facilitate mechanically and/or electrically synchronous contractions for resynchronization or to maintain synchrony during ventricular pacing. Specific implementations relate to such pacing for treatment of bradycardia.

According to one implementation, a patient is treated by directly stimulating the normal physiologic conduction system of the heart to elicit a conduction sequence. The conduction sequence follows the conduction sequence found in a normal heart, both spatially and temporarily. The degree to which the conduction sequence follows the that of a normal heart can be effected by the state of the myocytes, current composition of the extracellular matrix, magnitude, number and distribution of scar tissue due to infarcts, ischemic areas due to coronary obstructions to cardiac blood flow and the status of the myocardial substrate in general.

Aspects of the present invention build upon the discovery relating to simultaneously or nearly simultaneously (within 1-20 ms) applying two opposite polarity waveforms (pulse width between 0.01 to 5 ms) to two electrodes with respect to a reference, also referred to as an XSTIM waveform. It has been discovered that it is possible to, not only penetrate the root of the His Bundle and Purkinje system, but also to reach regions of the His after its bifurcation in the multiple bundles. The penetration of the multiple bundles generates a relatively normal conduction response through the right ventricle, the left ventricle and the septum. This allows for electrically activation of distal bundles at a point that allows bypassing of many conduction defects of the normal physiologic conduction system of the ventricles.

One embodiment of the present invention is directed to a cardiac rhythm therapy (CRT) method, system or device for dual ventricular pacing (also known as a biventricular pacing device) using two pacing signals each having a positive and negative component that has been modified for single ventricular pacing (if the device is a dual chamber biventricular device that has the capability of atrial sensing and pacing, that aspect of the device can be left intact). A first output is provided for connecting to a pacing lead; a second output is provided for connecting to a pacing lead; and a third output is provided for connection to a reference point. The reference point can be the conductive can of the device or an electrode on any other lead connected to the device. For instance, the reference point could be the distal or proximal defibrillation coil of a defibrillation lead, where the defibrillator device has been modified to implement the XSTIM right ventricular waveform configuration. Electrical circuitry is provided for connecting the second electrical connection to the first output, the third electrical connection to the second output, and the first and fourth electrical connections to the third output. If the device has the capability to sense and pace the atrium, the atrial sensing and pacing outputs can remain connected to the atrial lead.

Aspects of the present invention are directed to a pacing system having a signal generator that provides a first pacing signal and a second pacing signal, each pacing signal having positive and negative signal components. A pacing lead paces a heart from a single chamber of the heart, the pacing lead having a first electrode and a second electrode. Circuitry routes at least some of the signal components of the two pacing signals to the pacing lead by connecting a positive component of a first pacing signal and a negative component of a second pacing signal to a common reference and by connecting the negative component of the first pacing signal to the first electrode and the positive component of the second pacing signal to the second electrode.

Aspects of the present invention can be used in connection with a biventricular cardiac resynchronization therapy (CRT) device that provides biventricular pacing using a first pacing signal and a second pacing signal, each pacing signal having a positive and a negative signal component. Second and third outputs are connected to a reference point. First and fourth outputs are connected to respective inputs of the pacing lead. The positive component of a first pacing signal is provided to the first output and the negative component of the first pacing signal is provided to the second output and the positive component of the second pacing signal is provided to the third output and the negative component of the second pacing signal is provided to the fourth output.

According to an example embodiment of the present invention, a cardiac resynchronization therapy (CRT) device is improved upon. The unimproved CRT device provides biventricular pacing using a first pacing signal for one chamber of a heart and a second pacing signal for another chamber of the heart. The CRT device is improved by adding circuitry for referencing each pacing signal to a common reference component; and a pacing lead for using the CRT device to provide single chamber pacing using a negative component from one pacing signal and a positive component from the other pacing signal to pace the single chamber, wherein the pacing signal includes a negative pulse and a positive pulse, each referenced to the common reference component.

Aspects of the present invention are directed toward a circuit for use with a cardiac resynchronization therapy (CRT) device designed for biventricular pacing using a first pacing signal having a positive component provided to a first electrical connection and negative component provided to a second electrical connection and a second pacing signal with a positive component provided to a third electrical connection and negative component provided to a fourth electrical connection. The circuit includes a first output for connecting to a pacing lead, a second output for connecting to the pacing lead; a third output for connection to a reference point, and electrical circuitry connecting the second electrical connection to the first output, the third electrical connection to the second output, and the first and fourth electrical connections to the third output.

Another embodiment of the present invention relates to a device for connecting a pacing lead to a cardiac rhythm therapy (CRT) apparatus designed for dual chamber pacing using two pacing signals each having positive and negative signal components, the positive component of a first pacing signal being provided to a first output and the negative component of the first pacing signal being provided to a second output and the positive component of the second pacing signal being provided to a third output and the negative component of the second pacing signal being provided to a fourth output wherein, for dual chamber pacing, the first and second outputs are for use with a first pacing lead and the third and fourth outputs are for use by a second pacing lead. The interface includes a connector housing for physically mating with two interfaces of the CRT apparatus. The first interface provides the first and second signal components and the second interface provides the third and fourth signal components, each interface arranged for physically mating with a pacing lead. The housing also mates with a single pacing lead. The device includes electrical connections from the second and third outputs to a reference point and from the first and fourth outputs to respective inputs of the single pacing lead, thereby allowing single chamber pacing using the single pacing lead.

Aspects of the present invention are directed toward a method of creating a pacing system from a cardiac rhythm therapy (CRT) device having a signal generator that provides a first pacing signal and a second pacing signal, each pacing signal having respective positive and negative signal components. A pacing lead is provided for delivering pacing to a chamber of a heart, the pacing lead having a first electrode and a second electrode. The signal components of the two pacing signals are connected to the pacing lead by connecting a positive component of a first pacing signal and a negative component of a second pacing signal to a common reference and by connecting the negative component of the first pacing signal to the first electrode and the positive component of the second pacing signal to the second electrode.

An embodiment of the present invention is directed to a method of manufacturing a pacing system. A signal generator is produced that provides a first pacing signal and a second pacing signal, each pacing signal having respective positive and negative signal components. A pacing lead is produced for delivering pacing to a chamber of a heart, the pacing lead having a first electrode and a second electrode. Circuitry is produced for routing the signal components of the two pacing signals to the pacing lead by connecting a positive component of a first pacing signal and a negative component of a second pacing signal to a common reference and by connecting the negative component of the first pacing signal to the first electrode and the positive component of the second pacing signal to the second electrode.

Aspects of the present invention are directed toward a signal routing matrix for connecting a pacing lead to a cardiac rhythm therapy (CRT) device designed for dual chamber pacing using two pacing signals each having positive and negative signal components, the positive component of a first pacing signal being provided to a first output and the negative component of the first pacing signal being provided to a second output and the positive component of the second pacing signal being provided to a third output and the negative component of the second pacing signal being provided to a fourth output wherein for dual chamber pacing the first and second outputs are for use with a first pacing lead and the third and fourth outputs are for use by a second pacing lead. The signal routing matrix includes electrical connections from the second and third outputs to a reference point and from the first and fourth outputs to respective inputs of a single pacing lead, thereby allowing single chamber pacing using the single pacing lead.

As previously indicated, the above-discussed aspects and examples are not to be treated as limiting the scope or teachings of the disclosure herein. The skilled artisan would appreciate that, partly based on the various discoveries identified herein, the present invention can be embodied in many ways including but not limited to the above-discussed aspects and examples.

BRIEF DESCRIPTION OF THE DRAWINGS

The present invention may be more completely understood in consideration of a detailed discussion of various example embodiments, described in accordance with the present invention, as presented hereinafter in connection with the following figures, each of which is consistent with the present invention:

FIG. 8 shows an illustration a Biventricular DDD CRT device, consistent with an example embodiment of the present invention.

Figure 1A:
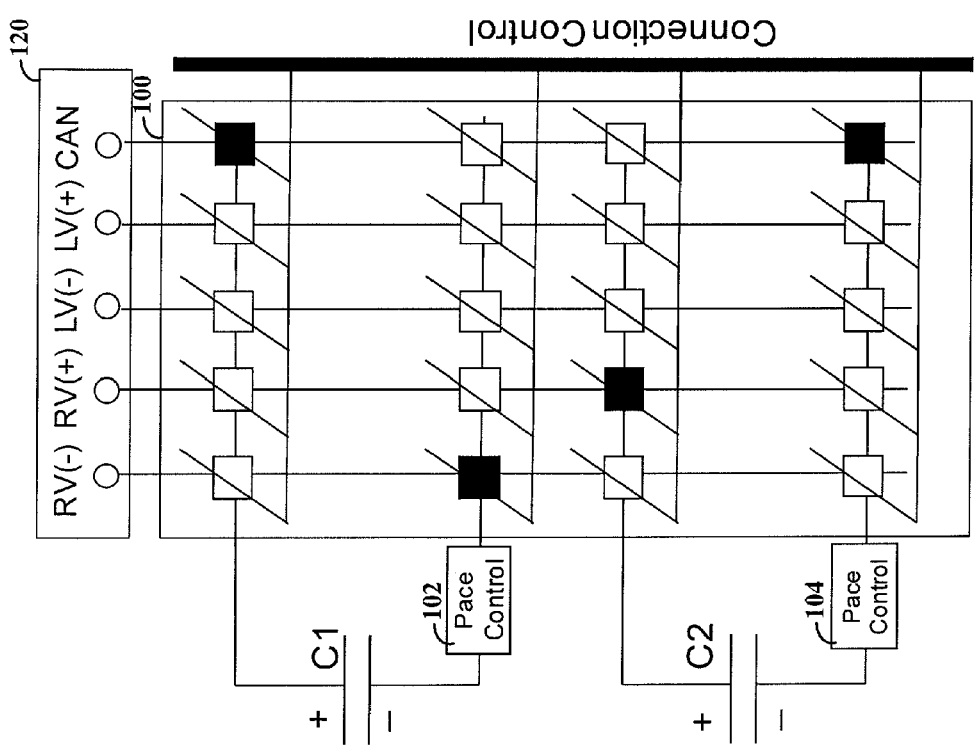
FIG. 1A shows an illustration of a modified CRT device, consistent with an example embodiment of the present invention.

While the invention is amenable to various modifications and alternative forms, various embodiments have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for maintaining and re-establishing a normal conduction of the activation sequence of the ventricles, both its spatial and time distributions from a lead in the right ventricle that has electrodes positioned behind the root of the septal leaflet of the tricuspid valve. The exact spot depends on the location of the block that needs to be bypassed. This spot can be dependent upon the location of the bundle fibers that are interrupting the conduction circuit and creating the abnormality. In many patients this location is close to the septal leaflet of the tricuspid valve and the fibrous atrio-ventricular and interventricular septum. While the present invention is not necessarily limited to such applications, various aspects of the invention may be appreciated through a discussion of various examples using this context.

It has been discovered that various aspects of the invention, including methods and devices, facilitate the deep penetration into the His root and distal Bundles. This penetration can include the left bundle and its bifurcations, the right bundle and its bifurcations and the septal bundle. This can be particularly useful for electrically bypassing various types of bundle branch blocks (e.g., right bundle branch block RBBB, proximal and distal; left bundle branch block LBBB, proximal and distal; left anterior hemiblock LAHB, proximal and distal, left posterior hemiblock LPHB, proximal and distal, intraventricular conduction defects IVCD, RBBB with left axis deviations and many other kinds of complex conduction defects). One such aspect of the invention is directed to the ability and use of waveforms, such as XSTIM, to penetrate deeply into the conduction system near the His Bundle. For example, the use of an XSTIM waveform creates a larger virtual electrode than with other waveforms and can be useful to overcome capacitance of the body.

The conduction system near the His Bundle can be thought of as a group of multiple electrical conductors each surrounded by electrical isolators. Thus, pacing signals introduced to the conduction system can be effected by capacitance between the electrical conductors. The electrical conductors are able to conduct the electrical impulse longitudinally from cell to cell, but there is very little conductivity, within the bundles, in the transversal direction. However, it is believed that strategically located bridges between cells allow the electrical stimulus to jump from one bundle to the other. This mechanism is believed to provide some redundancy in case a particular bundle stops working, for instance due to an infarct or micro-infarct. The bundles branch into sets of multiple conduction fibers as they progress towards their destination at the Purkinje fibers. The sets of fibers are electrically isolated from the rest of the myocardium by specialized tissue to prevent electrical depolarization of the surrounding myocytes from electrical pulses passing through the specialized conduction system. It is believed that this combination of electrical conductors and isolators effectively creates a distributed capacitor network, with, in its transversal cut, the bundle of His being in the middle of at least two serial capacitors. Because the cell membranes of the His bundle cells are also isolators, the intracellular fluid inside the His bundle cells are placed inside still another capacitor.

The XSTIM waveform provides a relatively large virtual electrode, whose asymmetrical dog bone shape will be affected by the polarity of the waveform, henceforth allowing the penetration of the waveform to be adjusted by modifying the relative polarities applied to the two electrodes. The XSTIM waveform also provides a high frequency stimulation energy that is able to bypass the capacitors. Thus, it is believed that the XSTIM waveform is able to deeply penetrate the His bundle. Even when the two opposite polarity pulses are separated by a few milliseconds (0 to 20 ms), the waveform is seen to penetrate and reach the bundles, even distal bundles, previously thought to be unreachable.

Furthermore, it has been discovered through experimental data that there is not a single capture threshold for the myocardium and for the His bundle. Indeed the response in many patients varies as the pacing voltage is increased. When the XSTIM amplitude is gradually increased from subthreshold values a first capture (previous art) threshold is found that triggers a depolarization sequence that activates the ventricles. In many patients this is followed by a second threshold that triggers the capture of some fibers of the His bundle. In patients with ventricular conductions defects, a continuous change in the electrocardiogram (ECG), QRS width, level of fractionation and vector of the 12 lead ECG is observed when the XSTIM amplitude is increased further. At some point a saturation point is reached and little or no further improvement is seen. It is believed that through careful positioning and selection of amplitude level, the pacing stimulus is able to reach the furthest blocked fibers of the conduction system, thus improving the coordination of the contraction to near normal levels.

The ability to achieve a normal conduction response may depend on the health of the substrate including, but not limited to, number of infarcts, myocytes degeneration, availability of mitochondria, blood supply, presence of interstitial fibrosis, degradation of the metallo-proteinase matrix, etc. The implication of these and other findings is that a similar effect can be achieved with a variety of wave-shapes and electrode configurations designed to traverse the capacitive networks (e.g., due to high frequency signal components).

The effective capacitance is lower for higher frequency components, including frequency components that are sufficient to trigger an action potential (0.01 to 20 ms). While some waveforms may be less efficient and use more energy to achieve similar results, the invention is not limited to applications of the most efficient waveforms.

Aspects of the present invention relate to the discovery that the distal blocks of the bundle of His can be bypassed using proximal stimulation of the bundles. For instances, such blocks can be bypassed by applying the appropriate electrical energy (pacing pulse) to a region of the His bundle. This region is located proximal to the tricuspid annulus and passes directly behind the septal leaflet of the tricuspid valve on the right ventricular side. This same region can be reached from the right atrium on the atrial side of the tricuspid valve by the root of the septal leaflet of the tricuspid valve.

Other aspects of the invention relate to the use of a high-amplitude (20-36 Volts) unipolar or bipolar pulse applied to the region. For instance, a unipolar pulse can be applied between the two electrodes located in the region of His and also allows for penetration that is deep enough to activate many fibers of the conduction system. Generally, the voltage required is much higher on the average than the energy required for an XSTIM pacing signal. Furthermore, results of human studies suggest that these high voltage pulses are felt by the patients and in certain cases they can cause undesired muscle contractions.

Aspects of the present invention are directed to modification of existing devices (e.g., those used for Bradyarrhythmia (pacemakers), Tachyarrhythmia (defibrillators—ICD) and Heart Failure (Cardiac Resynchronizers that deliver Cardiac Resynchronization Therapy—CRT)) into devices that can implement the XSTIM waveform and Electrical Bypass Therapy, either alone or in combination with CRT or ICD or CRT+ICD.

Normally the activation sequence of the ventricles starts in the atrial side of the atrio-ventricular node and propagates to the root of the His Bundle, where it bifurcates into a multitude of small bundles that are grouped into the right and left bundles. The fibers within each bundle are generally insulated from one another; however, there are locations exhibiting lesser insulation at intervals along the bundle. These bundles are electrically isolated from the surrounding tissue and terminate into the Purkinje cells that are in charge of communicating the electrical activation to the myocytes. A normal heart conducts an electrical signal from the His Bundle throughout the ventricles in around 60-70 ms. Conduction abnormalities, such as those due to infarct or micro-infarcts, can impede or block the conduction of the electrical activation impulse through the specialized His fibers. Such blocks result in Purkinje cells that do not receive the electrical activation impulse over the conduction fibers. The myocytes that are normally stimulated by these Purkinje cells are therefore not stimulated in the normal fashion. Instead, these myocytes are stimulated from electrical signals propagating through myocytes that did receive the electrical activation pulse from the conduction fibers. The conduction velocity between myocytes is significantly slower than the conduction velocity of the conduction fibers. For example, the conduction fibers have a conduction velocity of around 2 m/s whereas the cell to cell conduction velocity of myocytes is around 0.5 m/s. Accordingly, these blocks can significantly distort both the spatial and time distributions of the electrical activation of the ventricles. These temporal and spatial activation sequence distortions introduce mechanical asynchronies that can adversely affect the hemodynamics of the heart. Such mechanical asynchronies can lead to a set of progressive mal-adaptive compensatory processes, among them dilatation, in the late activated regions: fibroblast proliferation, local proto-oncogene activations, compensatory regional hypertrophy, sympathetic/parasympathetic balance increases, among others. These processes can lead to heart failure that may have been delayed or prevented had the conduction abnormalities not being there to start with. Therefore, according to aspects of the present invention, both maintaining (when ventricular pacing is required due to bradycardia) or re-establishing a normal conduction sequence (or as normal as possible if the substrate is already degraded due to infarcts, micro-infarcts, amyloidosis, Chagas disease, advanced dilatation and degradation of the metalloproteinase support matrix of the myocytes, myocytes degradation, etc.) can have significant advantages for delaying, stopping or even reversing the progression towards Heart Failure.

For other forms of resynchronization therapy the activation sequence is started from two sites in the right and left ventricles to directly stimulate the myocytes rather than use the normal the conduction system. This leads to abnormal activation sequences. In one implementation, physicians are directed to place at least one lead in the epicardium of the left ventricle (e.g., by placing this lead in the coronary vein system of the left ventricle). This placement creates a further type of asynchrony as the activation sequence will not only be slow but also inverted with respect to a normal/healthy sequence. Despite these problems of such treatment, this type of the cell to cell (without the activation of the conduction system) activation sequence is better than the other applications of CRT. The success rate of CRT using biventricular pacing is limited to only about 60 to 70% of patients where the untreated activation sequence is "worse" than the new artificial sequence created by biventricular pacing.

Therefore, aspects of the present invention are useful for providing a modality of resynchronizing the ventricles and can be easily implemented. For example, embodiments of the present invention relate to a method that does not require the step of placing a lead in the LV through the coronary sinus into the LV cardiac veins something that could only be achieved by highly specialized physicians in only high complexity institutions and after long, expensive and sophisticated training. Moreover, embodiments of the present invention can safely (e.g., one less lead that can fail or cause problems) provide pacing benefits to patients that would not otherwise have viable treatment options.

In certain implementations, the invention is used to facilitate mechanically and/or electrically synchronous contractions for resynchronization (possibly due to conduction abnormalities such as Left Bundle Branch Block (LBBB)) where, responsive to aspects of the invention, the left ventricle has regained its ability to rapidly contract and/or to synchronize contractions of cardiac muscle of the septum and respective free wall(s). While the present invention is not necessarily limited to such applications, various aspects of the invention may be appreciated through a discussion of various examples using this context.

Consistent with specific embodiments and various discoveries realized in connection with the present invention, heart function can be improved by pace-mapping and/or by delivering pulses to a cardiac site. The heart function is indicated or measured using a variety of techniques. Representative examples include, but are not limited to, measuring/detecting: a narrowing of the QRS width, decreased level of QRS fractionation in the 12 lead ECG, normalization or improvement of the vector angle of the 12 lead ECG, decrease in the late LV activation timing, improvement in the mechanical synchronicity of free wall and septal wall, improvement in the rate of increase of left ventricular pressure, improvements in hemodynamics indirectly assessed from right ventricular pressure measurements, a decrease in the left ventricular end diastolic pressure, improvements in the effective pressure, improvements in the heart sounds, disappearance of the S3 component of the heart sounds, improvement in the acceleration profile of the heart as evaluated with an accelerometer, improvement in efficiency of the contraction (amount of energy spent per 100 ml of blood ejected), improvement in the respiratory profile of the patient or his/her minute ventilation as assessed with impedance or other techniques, an increased parasympathetic/sympathetic balance, improvements in the heart rate variability profile, improvements in the percentage of time the patient is active, improvements in the level of lung edema as assessed by the impedance technique, and/or by any combination thereof. In specific implementations, the pacing can be implemented using XSTIM waveform at a target pacing region.

A variety of sensing devices can be used to assess the efficacy of the pacing signal and location. Examples of suitable sensors include, but are not limited to sensors that can be used to: assess the dP/dt max (maximum rate of increase of left intraventricular pressure, directly measured or indirectly derived from echo-techniques or right ventricular pressure measurements), cardiac output, electrocardiographs can be used to quantify the narrowing of the QRS width, decreased level of QRS fractionation in the 12 lead ECG. Other examples include, but are not limited to, the following devices or sensed heart-functionality: vectocardiographs or body surface mapping equipment can be used to assess the normalization or improvement of the vector angle of the 12 lead ECG, decrease in the late LV activation timing, improvement in the mechanical synchronicity of free wall and septal wall, many methods and equipment exist to assess the improvement in the rate of increase of left ventricular pressure both directly or indirectly, implantable or external sensors can be used to assess the improvements in hemodynamics indirectly from right ventricular pressure, and/or a decrease in the left ventricular end diastolic pressure, and/or improvements in the effective pressure, microphones and heart sounds quantification equipment can be used to assess the improvements in the heart sounds, disappearance of the S3 component of the heart sounds, an accelerometer either implanted, inside the patient (i.e., in the tip of a lead) or on the surface of the body can be used to assess the improvement in the acceleration profile of the heart, intracardiac temperature can be used among other techniques to assess the improvement in efficiency of the contraction (amount of energy spent per 100 ml of blood ejected), transthoracic impedance measurements or intracardiac lead impedance measurements can be used to assess the improvement of the respiratory profile of the patient or his/her minute ventilation, Heart Rate variability analysis can be used to assess an increased arasympathetic/sympathetic balance and/or general improvements in the heart rate variability profile, an implantable accelerometer can be used to assess the improvements in the percentage of time the patient is active, transthoracic or lead impedance can be used to assess improvements in the level of lung edema, and/or any combination thereof. These and other aspects can be directly measured or using indirect non-invasive measurements like cuff based estimations of the systolic and diastolic arterial pressure, with an increase in the systolic pressure or a decrease of the diastolic pressure and with no change of the systolic being the goal. Another indirect method of estimating includes extrapolation of relevant hemodynamic information from right ventricular pressures.

Aspects of the invention are directed to locating and/or pacing at a target pacing region. In one implementation, the target pacing region is at or near the His Bundle. In specific implementations, locating the target pacing region can be assisted by determining a likely location of the blocked fibers. This can be accomplished using anatomical knowledge and extrapolation to 2-dimensional fluoroscopy. A pacing catheter can be placed near the determined location for delivery of the pacing signals. A sensor, such as a 12 lead ECG detecting improved/normal QRS and activation vector possible for the patient, is used to locate the optimum application site.

According to one embodiment of the present invention, a pre-shaped sheath or a steerable or a deflectable sheath with a pair of electrodes on its tip is used for pace-mapping. Once the optimal application site is determined, the permanent pacing catheter is introduced to the site identified by the sheath, without moving its tip, and the catheter is then fixed to the location, e.g., by screwing into the septal wall. The parameters of the device, such as atrio-ventricular delay (the time from the sensed atrial event till the issuance of a pacing stimulus in the optimum site), the pacing (e.g., XSTIM) amplitude, the interpulse distance (from −20 ms for the first pulse to the second opposite polarity pulse to +20 ms), the polarity of the pulses (either − to tip or + to tip), the order of the polarities if the interpulse distance is more than zero (− first or + first) can be optimized in one embodiment using indirectly derived electrocardiograms obtained from the electrodes present in the implanted leads (see above for other sensors that can also be used for site optimization). For background information on such implanting procedures, reference can be made to U.S. Pat. No. 7,299,086 to MaCabe et al., Wireless ECG in implantable devices and issued on Nov. 20, 2007, which is fully incorporated herein by reference.

In certain implementations, the optimization can be performed by implanting a right ventricular pressure sensor to sense direct right ventricular pressure measurements. Such a sensor can detect right ventricular systolic pressure. This detection can be used to extrapolate left ventricular responses, such as left ventricular systolic pressure or preferably dP/dtmax or left ventricular end-diastolic pressure (LVEDP). To ensure hemodynamic stability, these measurements can be performed during periods when the patient is at rest. The atrial rate can be monitored and when it is discovered that a period of low and stable rate occurs other sensors can be used (i.e. an accelerometer to determine that the patient is still or doing minimal movements). These measurements taken during a stable rate are then used to adjust the parameters of the pulse generator and/or placement. The parameter adjustment can be automatically implemented by the device after the implant has been completed, for instance it can be accomplished in a standard dicotomic way, where the starting point is the previous point and the parameter is adjusted up by 10-30%. If no different effect is seen the parameter is adjusted 10-30% down. If a beneficial effect is seen, the parameter is then adjusted further down by 10-30% until a detrimental effect is seen, at that point the last adjustment is cut in half and the parameter adjusted up by 5-15% and measurements taken again. If the effect is still detrimental, the parameter is adjusted up by 2.5-7.5% until a beneficial effect is seen. The adjustment will then naturally converge to the optimum parameters.

According to another embodiment, in patients with dilated hearts, the physician may choose to give preference to the heart as an organ, rather than to the rest of the body, to facilitate healing and reverse remodeling of the heart. For that purpose, the preload of the left ventricle can be reduced while keeping the heart synchronous using pacing, such as XSTIM, at the optimum site. This differs from some of the methods discussed herein where the parameters were adjusted to find optimal left ventricular function so as to find the point of functioning where the heart was providing a high level of cardiac output to the body. This type of optimization, however, can be less than optimal with respect to the effect on the heart. Aspects of the present invention allow the maintenance of ventricular synchrony for a variety of different AV delays. For example, the ability of XSTIM CRT to maintain synchrony at various AV delays allows for the use of AV delays that are beneficial for the dilated heart, even where the AV delays are suboptimal for preload of the left ventricle. Therefore, for patients with extremely dilated hearts, the AV delay can be set to a very short delay. The AV delay can be determined by reducing the AV delay until the left atrial contraction starts occurring after the closure of the mitral valve. This event represents the shortest possible AV delay that will not compromise lung function by increasing pulmonary capillary wedge pressure. At the same time this AV delay will allow the heart to function with the lowest possible end diastolic pressure and preload. These measurements can be easily done using current art Doppler echocardiography. Optimizing the AV delay in the manner taught in this disclosure can allow the heart to work with a low preload to increase the likelihood of reverse remodeling. After the heart shows improvement/reverse-remodels, the AV delay can be increased to a setting that is set according to the previously mentioned techniques (e.g., ECG, RV pressure, LV dP/dt, ECG measurements, LVEDP, etc.).

In an embodiment of the present invention, the AV delay setting is started at a very low AV delay determined by the implanting physician, using an estimate, patient symptoms or Doppler echocardiography as described above. After a predetermined amount of time (ranging from weeks to months, programmable by the physician), the device can be set to automatically switch the AV delay of the implantable device to improve global hemodynamic function. Alternatively, less complex devices could be programmed with an initial, short delay. The device also is programmed with a long AV delay target, which is obtained by slowly increasing the AV delay from the short value to the long value determined by the physician in the time period established by the physician using clinical judgment.

Certain methods and specific aspects consistent with these and other embodiments of the present invention concern directing a catheter-type device for delivering pulses to a cardiac site where the improved heart function involves: determining a pacing (voltage) threshold, beyond the capture threshold, to improve heart function; delivering pulses of opposite polarity to achieve such heart-function improvement; delivering pulses of opposite polarity at a site near the His bundle; electrode-based His-pacing, without necessarily penetrating into the His bundle; generating and/or delivering multiple pacing profiles, e.g., by iterating through different pacing profiles, including a pacing profile that delivers pulses of opposite polarity and another pacing profile; delivering a pacing profile to generate a synchronous contraction of the septal wall and free wall of the LV from a RV (right-ventricle) pacing location; and treating one or more of distal BBB (bundle branch blocks) and/or diffuse BBB by pacing at a site near the root of the His bundle.

Various embodiments of the present invention include stimulation catheters, systems and methods that employ two or three electrodes. In specific embodiments of the present invention, the most distal two electrodes are located at the tip of the catheter. According to a specific implementation, the distal two electrodes are separated by 4 mm and the electrodes are implemented as a 2 mm thick ring in a 4 French catheter and a 4 mm radius half sphere in the tip of the catheter. An optional third electrode can be located in a number of places, such as on the lead body some distance from the first pair or even located between the pairs. An intravenous location for the reference electrode can be used where the time separating the two opposite polarity pulses is not zero. This can be useful to reduce the likelihood of pocket stimulation.

As a specific example of an unexpected result, it has been discovered that His bundle pacing and/or para-Hisian pacing can be used to treat patients exhibiting a variety of cardiac abnormalities previously thought to be unsuitable for His bundle pacing (e.g., large QRS complexes due to distal left bundle blocks or diffuse left bundle blocks). It has also been discovered that implantation complexities (e.g., duration and/or invasiveness) can be beneficially affected by the use of specific devices, systems and placement methods.

According to an example embodiment of the present invention, a specialized stimulation profile is used to capture a synchronous contraction of the left and right ventricles. The stimulation profile is provided to a lead in the right ventricle. The lead placement and stimulation profile are selected in response to sensed heart function during the pacing. In particular, the lead placement and stimulation profile are determined based upon more than whether the placement/profile results in capture (e.g., QRS width or late activation site timing). In certain instances, this can result in pacing voltages/profiles not otherwise believed to be desirable (e.g., voltages derived from criteria other than the capture threshold and/or His bundle pacing without penetrating the surrounding (fibrous) tissue with a pacing lead).

The understanding of various implementations of the present invention can be facilitated with a discussion of existing pacing, implantation and related procedures and devices. While a substantial number of differences exist between various embodiments of the present invention and such existing pacing, the present invention does not exclude implementations that include aspects of existing pacing. Quite to the contrary, aspects of the present invention are particularly useful for implementing in conjunction with existing pacing methods and devices. Accordingly, a number of embodiments of the present invention provide the flexibility to be useful when combined with existing implementations.

Aspects of the present invention facilitate the use of existing CRT device architecture as produced by a number of manufacturers to function for use with the newly discovered inventions of the underlying patent documents. These inventions include, but are not limited to, the use of XSTIM waveforms (two opposite polarity pulses used to capture a single contraction of the heart) to provide resynchronization therapy from a lead located in the right ventricle.

Current art Biventricular CRT (cardiac resynchronization therapy) devices have two independent ventricular channels, one for the RV and the other for the LV. Such CRT devices are often arranged to provide two negative-polarity pulses with programmable amplitude, pulse width and relative time delay. Aspects of the present invention facilitate the output of two opposite polarity pulses with programmable amplitude, pulse width and relative time delay (including no delay).

According to one embodiment of the present invention, modifications are made to Biventricular CRT devices that have flexible analog/digital chip design architecture allowing on-chip reconnections between different output terminals to the output circuitry. For example, XSTIM-capable devices can be produced through reprogramming switches/multiplexers used to define the electrical connections to one or more pacing leads.

FIG. 1A shows an illustration of one such modified CRT device, consistent with an example embodiment of the present invention. FIG. 1A shows two pacing capacitors C1 and C2 that provide pacing output signals for the ventricular channels. Pace Control 102 and 104 provide various functions for pacing delivery including, but not limited to, timing control, amplitude settings, and pulse duration. The connection grid 100 provides selectable connection between the pacing capacitors C1, C2 and the various outputs 120. The solid boxes of connection grid 100 represent connections between the capacitors C1, C2 and the output directly above. Thus, the positive signal component of C1 and the negative component of C2 are both connected to a reference, such as the can of the CRT device. The negative signal component of C1 is connected to one portion of the right ventricle (RV) lead and the positive signal component of C2 is connected to another portion of the right ventricle lead. In this configuration the right ventricle lead would be used to provide the pacing signal. It should be noted that a similar configuration could be implemented for what is conventionally thought of as the left ventricle lead, although the pacing would still preferably be applied to the right ventricle of the patient.

Accordingly, aspects of the invention involve a Biventricular CRT device configured to connect a first electrical connection (C1−) to a first output (RV−), a second electrical connection (C2+) to a second output (RV+), and the third (C1+) and fourth (C2−) electrical connections to a third output/reference.

FIG. 1A shows the connection grid 100 being configurable in response to a connection control circuit. The connection grid 100 shown in FIG. 1A is a relatively simple connection grid that allows each terminal to select between the five different outputs. More complex or simple connection grids can also be implemented, including a connection grid that allows for selection applying the pacing control to either or both terminals of the capacitors C1 and C2.

The specific circuit shown in FIG. 1A is merely representative of any number of configurable circuits that can be implemented in accordance with the present invention. For example, the power source for the pacing signals need not be capacitive per se and could be provided by various power providing circuits and electrical elements.

Although not shown, an atrial channel could also be included as part of the device; however, it could remain essentially identical between the Biventricular CRT device and the modified implementation discussed herein.

Figure 1B:
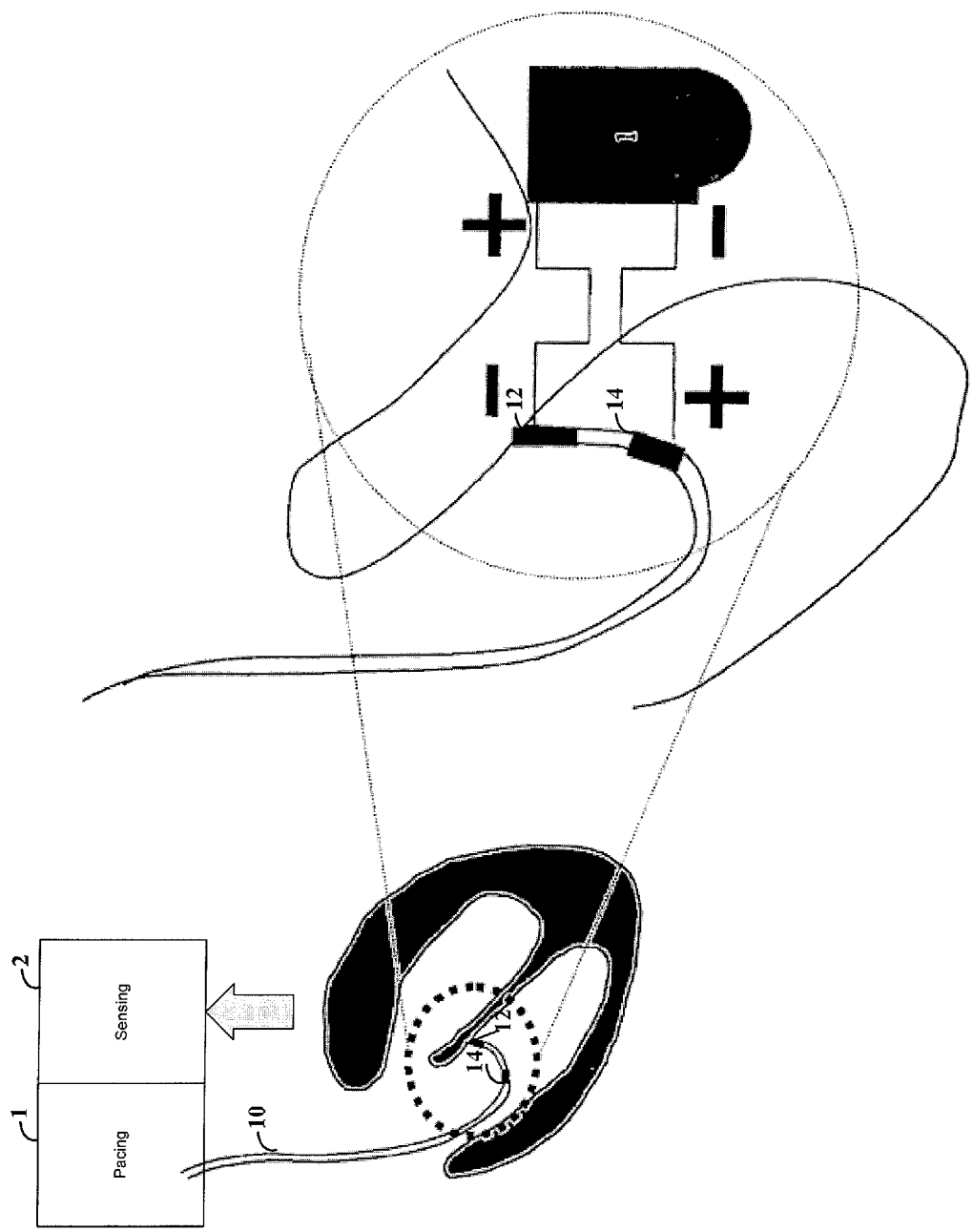
FIG. 1B shows an illustration of a CRT device, such as those modified in FIGS. 1A-8, placed within the heart, consistent with an example embodiment of the present invention.

FIG. 1B shows an illustration of a CRT device, such as those modified in FIGS. 1A-8, placed within the heart, consistent with an example embodiment of the present invention. A heart H is shown in a cross-section showing a right ventricle RV and a left ventricle LV divided by a septum S. A catheter is provided in the right ventricle RV with a distal electrode 12 secured to the septum and a proximal electrode 14 in the right ventricle. The right-hand side of the figure shows the catheter 10 enlarged and energized by pacemaker 1 to create two monopolar pulsewaves between electrodes 12, 14 and the pacemaker 1. The pulsewaves can be modified in as discussed herein including, but not limited to, phase, duration, amplitude and polarity configuration.

As discussed in U.S. patent application Ser. No. 11/300, 242, aspects of the present invention relate to a method of application and a way to facilitate the implantation and to avoid the connection and disconnection of the catheter 10. Sense circuit 2 can be used to check the proper placement and pulsewave configuration. In a specific embodiment a deflectable sheath with an electrode on its edge can be used. This allows stimulation to be applied in order to check the proper placement of the catheter (e.g., responsive to signals received by sense circuit 2) and for affixing (e.g., screwing into the heart) of the catheter into the proper place. The sheath, if used, can then be removed and is eventually disposable.

As discussed herein, the sense circuit 2 can be implemented according to any number of different sensing signals that represent heart function due to pacing signals delivered by a pacing generator.

According to a specific embodiment of the present invention, a pacemaker and a method of application are implemented as follows:

A pulse generator, single-chambered or dual-chambered has ventricular output including at least two superimposed monopolar pulsewaves of reversed polarity between each other, with programmable configuration, in respect to a neutral reference point. The neutral reference point can be, for example, the pacemaker's metallic box or a third electrode implemented as a tripolar catheter.

An active-fixation ventricular catheter.

A deflectable and/or pre-shaped sheath with a distal tip having an electrode.

Determining a stimulation place in the right interventricular septum (or otherwise near the His Bundle) using the sheath.

Where the determined stimulation place is such that pacing therefrom allows for a greater interventricular synchrony making the stimulation of the left ventricle easier, such as by the application of an electric alternative circuit principle or Electrical Bypass that reestablishes the physiological conduction of a damaged (e.g., conduction abnormality) heart.

The general aspects of FIG. 1B can be implemented in combination with one or more of the various embodiments disclosed herein including, but not limited to, aspects discussed in connection with each of the figures.

Figure 2:
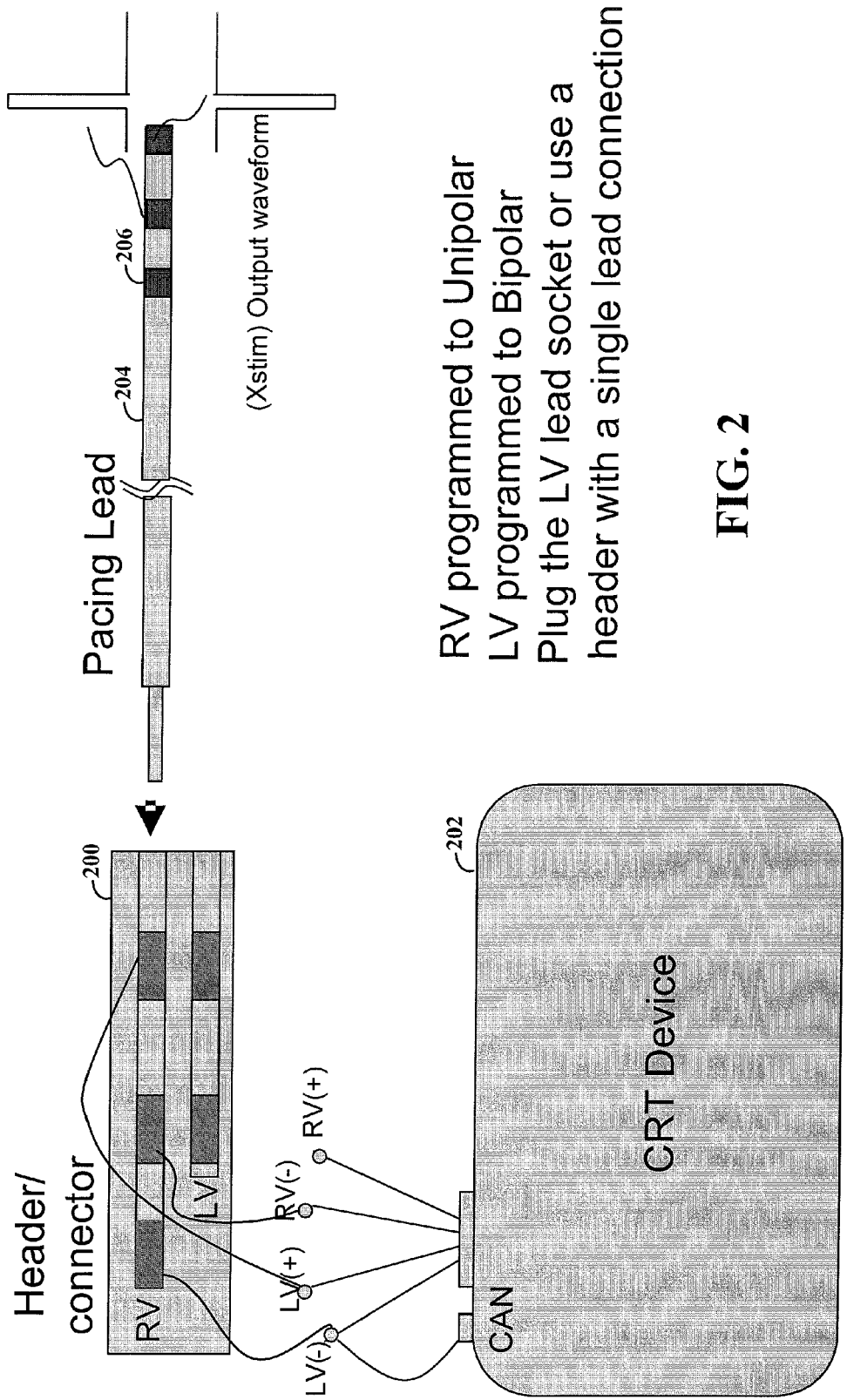
FIG. 2 shows an interface and circuit for providing a pacing signal, consistent with the present invention.

FIG. 2 shows an interface and circuit for providing a pacing signal, consistent with the present invention. Header/connecter 200 is a circuit and interface for connecting the outputs of CRT device 202 to a single pacing lead 204 (again an atrial channel could also be included). The connection lines between the outputs of CRT device 202 (RV+/− and LV+/−) and the header 200 show the connection functionality provided by the circuit of connector 200. Thus, the positive component of one of the RV and LV signals is connected to the pacing lead 204 and the negative component of the other of the RV and LV signals is also connected to the pacing lead 204.

The reference electrode 206 as placed on pacing lead 204 is an optional component. Another option is to use the can of the CRT device as a reference (alone or in combination with one or more reference points/electrodes). One or both of the other signal components (e.g., LV− or RV+) are connected to a reference component, such as the can of CRT device 202 and/or to a reference electrode 206 of the pacing lead 204. In this specific embodiment, the CRT is configured to provide RV signal as a unipolar pacing signal (since the RV(+) is not connected to the CAN/or electrode 206) and the LV signal as a bipolar pacing signal. Unipolar pacing signals use a single signal component, which can be referenced to the can of the device, to be delivered to the pacing site, whereas bipolar pacing signals use a signal component referenced to the other nearby electrode to be delivered to the pacing sites. In unipolar mode, the devices internal logic connects the (+) side of the signal to the can and the negative to the active electrode at the tip or ring (in case of LV leads) of the intracardiac leads.

According to another embodiment (not shown), the RV and LV leads can be reversed in their connections. The RV lead is then configured for bipolar pulse and the LV lead is configured for a unipolar pulse.

As shown by the signal waveforms, the pacing lead 204 can thus be configured to deliver two opposite polarity pulses, which can be simultaneously delivered or delivered with an offset between the pulses. This offset can be accomplished using the programmable interventricular delay of the device.

Figure 3:
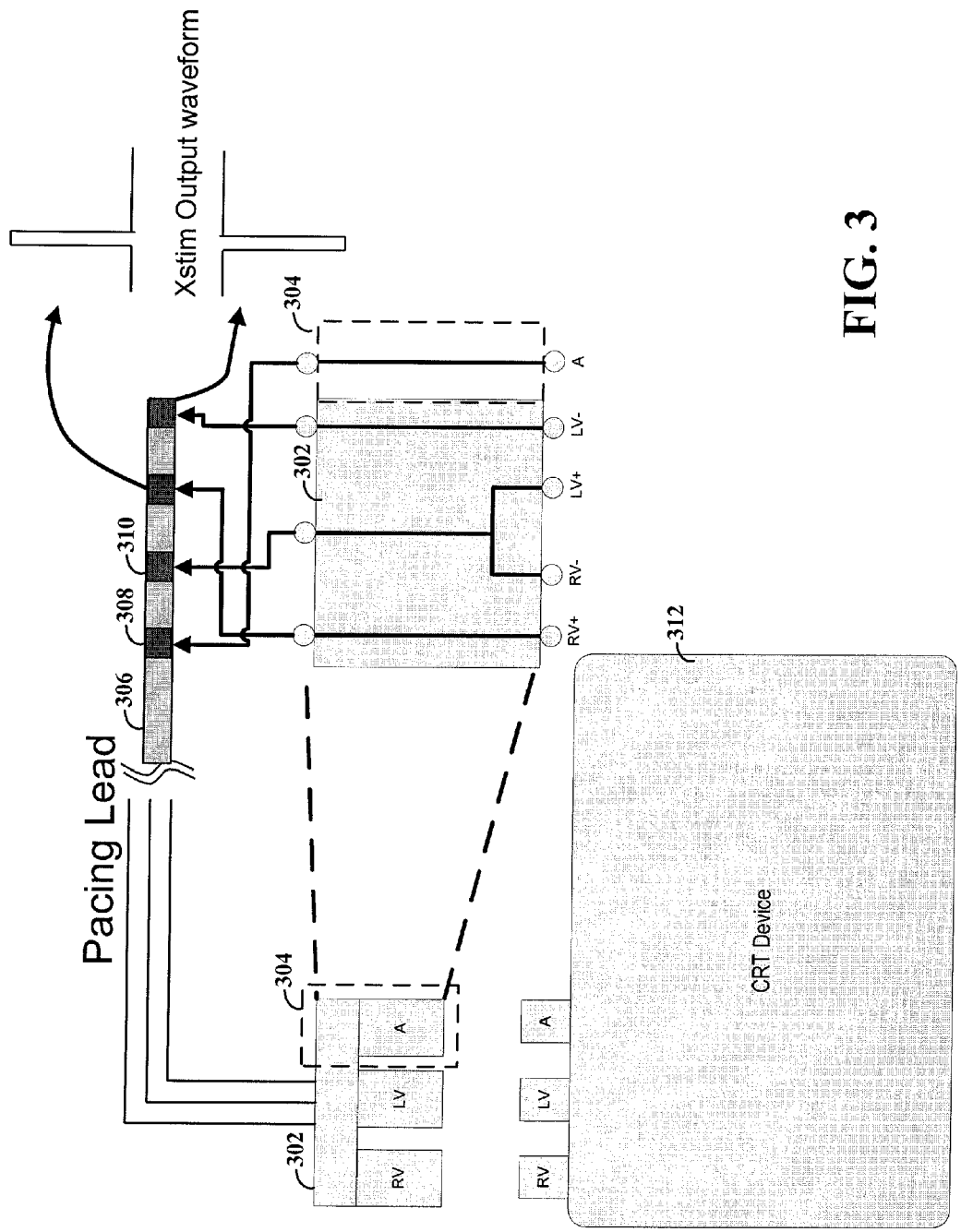
FIG. 3 shows an interface and circuit for providing pacing signals, consistent with embodiments of the present invention.

FIG. 3 shows an interface and circuit for providing pacing signals, consistent with embodiments of the present invention. Connector/interface 302 includes a circuit for routing signal components from CRT device 312. Optionally, atrial component 304 can be implemented. For example, atrial component 304 can be used to connect to an electrode 308, which can be located on pacing lead 306 or on a separate pacing lead, to atrial port A. This electrode can be used to sense heart function, such as atrial activation. RV+ and LV− are shown as connecting to respective leads for delivery of pacing signals. The polarities of the RV and LV signal components are merely exemplary and could be reversed. RV− and LV+ are shown as connecting to a reference, such as electrode 310. Optionally, the reference could be the can of CRT device 312, a remote reference point, or both. As discussed in connection with FIG. 2, CRT device 312 can be configured with one of the RV or LV signals providing a unipolar signal. For such an implementation, the reference component (e.g., LV+) could be left unconnected.

FIG. 3 also shows that the interface device can include a connector housing that is constructed to physically interface with two or more lead outputs of the CRT device 312. Specifically, the RV and LV outputs of CRT device 312 are designed to interface with respective leads. The connector/interface 302, however, can connect to multiple lead outputs of the CRT device and provide a single lead output, which can include connections to multiple outputs of the CRT device 312. Thus, the CRT device 312, although designed for interfacing with two or three pacing leads, can be used as a single pacing lead with little or no modifications. Similarly, the pacing lead can be implemented using a standard connection type, if so desired.

Although not shown, the polarities of ring and tip could be reversed. This can be useful for changing the shape of the virtual electrode around the physical electrodes. For example, the larger head of the dog-bone virtual electrode could be inverted to be directed towards the blocked regions of the His bundle. This can be particularly useful for correcting for small differences between the optimum site identified by the sheath and the actual placement of the implantable electrode. A rotation of the dog bone virtual electrode can be achieved by the relative timing and polarity of the two pulses (negative first, positive first, ring positive, tip positive and/or inter-pulse timing).

Although not explicitly shown, the connector/interface 302 can also be implemented for interfacing with additional outputs, including additional pacing outputs, such as those described in connection with FIG. 8.

Figure 4:
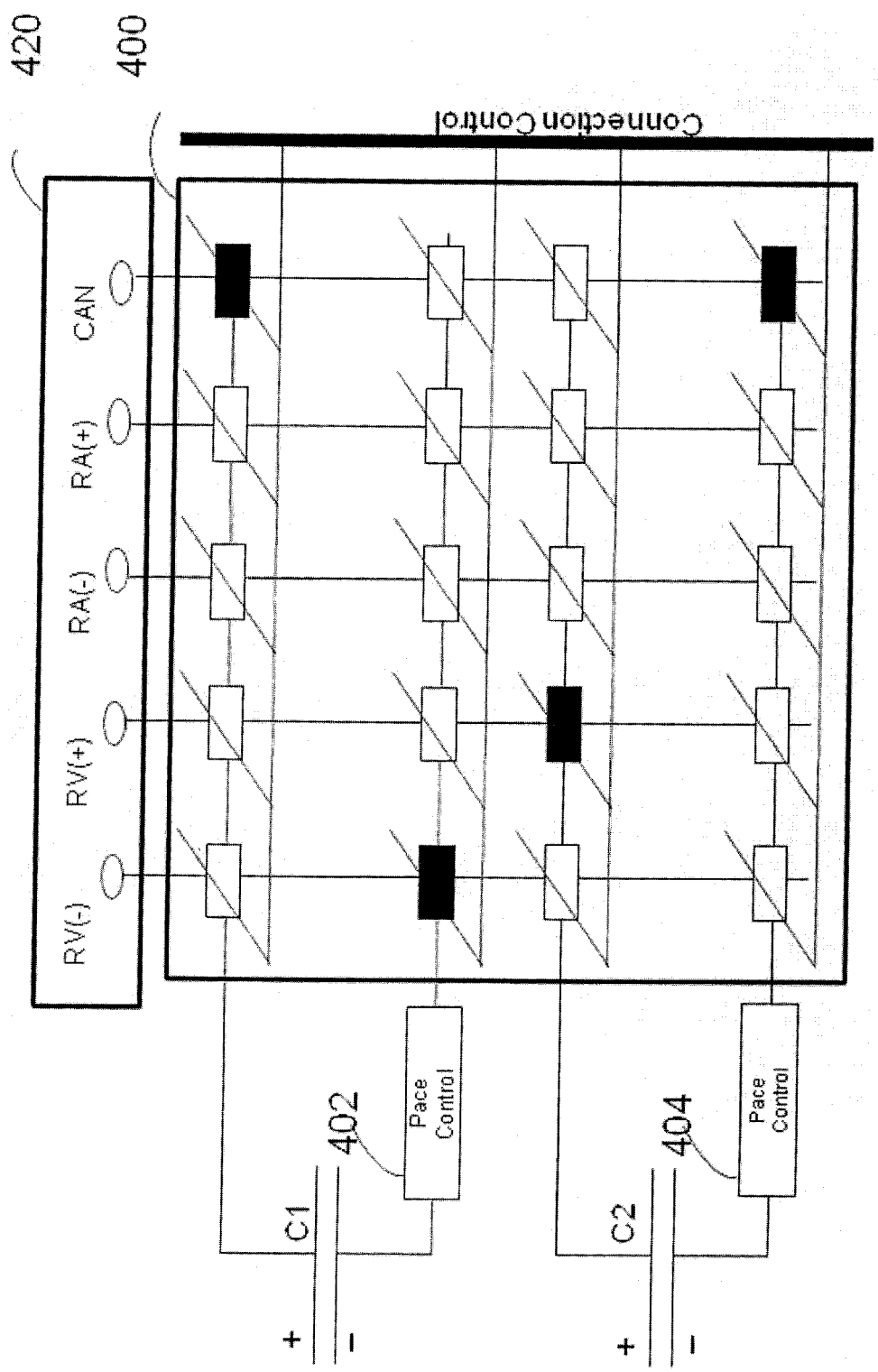
FIG. 4 shows an illustration of a modified dual chamber pacemaker (DDD) device, consistent with an example embodiment of the present invention.

FIG. 4 shows an illustration of a modified dual chamber pacemaker (DDD) device, consistent with an example embodiment of the present invention. FIG. 4 shows two pacing capacitors C1 and C2 that traditionally provide pacing output signals for the atrial and ventricular channels respectively. Pace Control 402 and 404 provide various functions for pacing delivery including, but not limited to, timing control, amplitude settings, and pulse duration. The connection grid 400 provides selectable connection between the pacing capacitors C1, C2 and the various outputs 420. The solid boxes of connection grid 400 represent connections between the capacitors C1, C2 and the output directly above. Thus, the positive signal component of C1 and the negative component of C2 are both connected to a reference, such as the can of the DDD device. The negative signal component of C1 is connected to one portion of the right ventricle (RV) lead and the positive signal component of C2 is connected to another portion of the right ventricle lead. In such a configuration the right ventricle lead could be used to provide the pacing signal and the atrial lead could be left disconnected. It should be noted that a similar configuration could be implemented for what is conventionally thought of as the right atrial lead, although the pacing would still preferably be applied to the right ventricle of the patient.

Accordingly, aspects of the invention involve a DDD device configured to connect a first electrical connection (C1−) to a first output (RV−), a second electrical connection (C2+) to a second output (RV+), and the third (C1+) and fourth (C2−) electrical connections to a third output/reference.

FIG. 4 shows the connection grid 400 being configurable in response to a connection control circuit. The connection grid 400 shown in FIG. 4 is a relatively simple connection grid that allows each terminal to select between the five different outputs. More complex or simple connection grids can also be implemented, including a connection grid that allows for selection applying the pacing control to either or both terminals of the capacitors C1 and C2.

The specific circuit shown in FIG. 4 is merely representative of any number of configurable circuits that can be implemented in accordance with the present invention. For example, the power source for the pacing signals need not be capacitive per se and could be provided by various power providing circuits and electrical elements.

Figure 5:
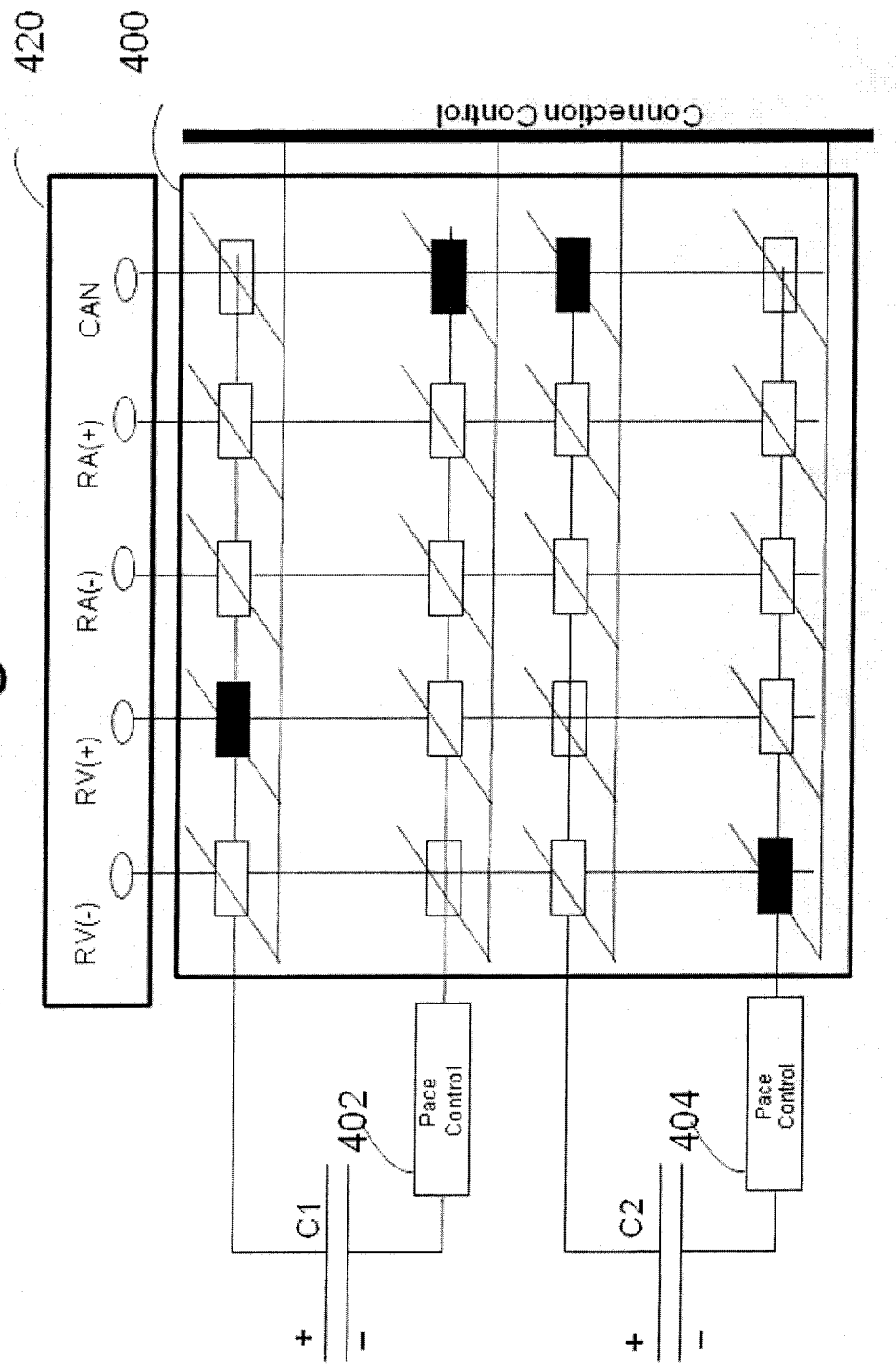
FIG. 5 shows an illustration of a modified dual chamber pacemaker (DDD) device, consistent with an example embodiment of the present invention.

FIG. 5 is similar to FIG. 4, however, the reference electrode(s) are connected to the negative of capacitor C1 and positive of capacitor C2, while the positive of C1 and negative of C2 are connected to the RV leads.

Figure 6:
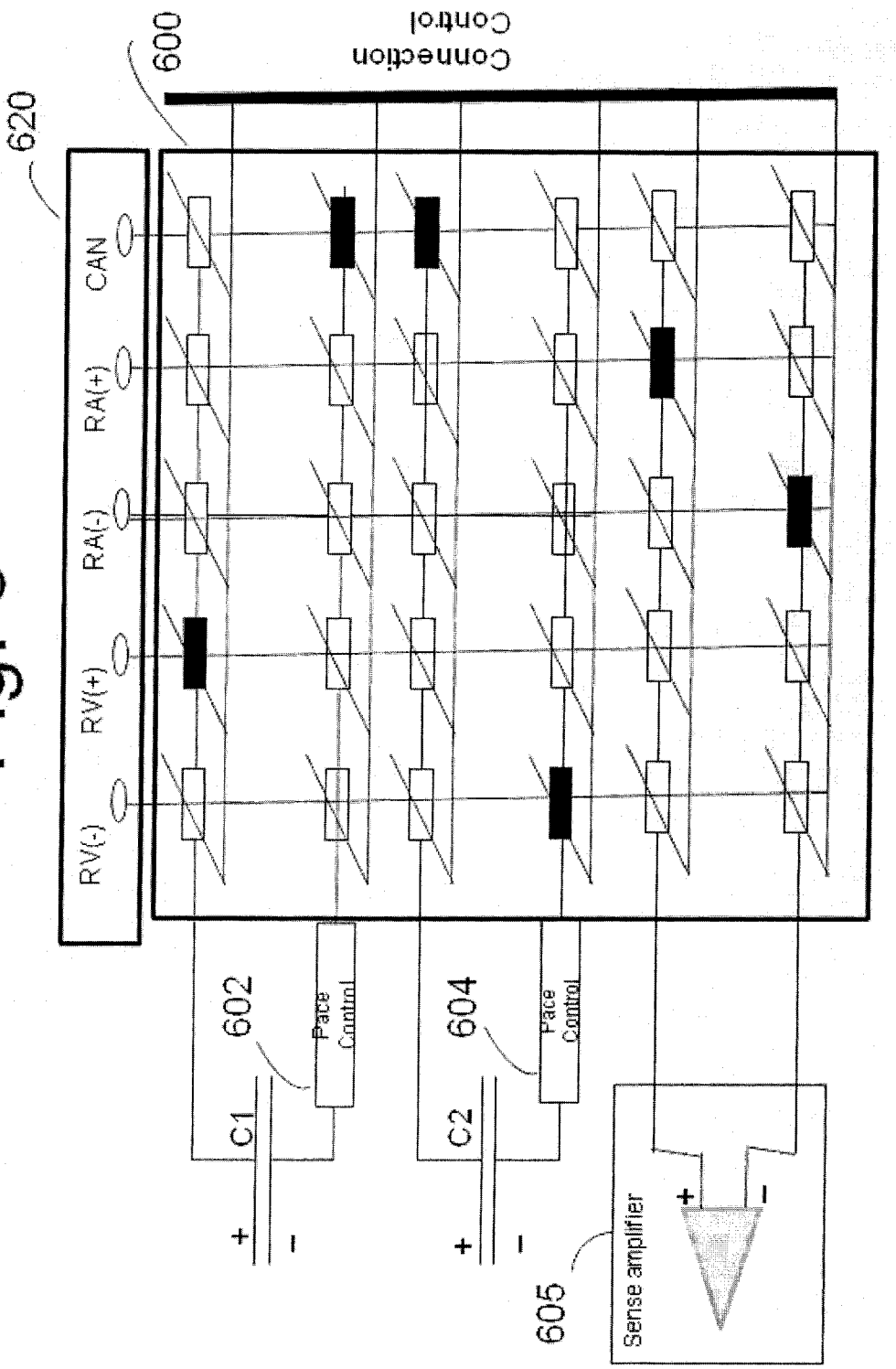
FIG. 6 shows an illustration of a modified DDD device, consistent with an example embodiment of the present invention.

FIG. 6 shows an illustration of a modified DDD device, consistent with an example embodiment of the present invention. FIG. 6 shows two pacing capacitors C1 and C2 that provide pacing output signals for the ventricular channels and sense amplifier 605. For simplicity, the sense amplifiers of the ventricular channel are not shown, however, should the sense amplifiers be implemented, they can be attached to the RV channel—between RV(−) and RV(+) for bipolar sensing and between RV(−) and Can for unipolar sensing. Pace Control 602 and 604 provide various functions for pacing delivery including, but not limited to, timing control, amplitude settings, and pulse duration. The connection grid 600 provides selectable connection between the pacing capacitors C1, C2 and the various outputs 620. The solid boxes of connection grid 600 represent connections between the capacitors C1, C2 and the output directly above. Thus, the negative signal component of C1 and the positive component of C2 are both connected to a reference, such as the can of the DDD device. The positive signal component of C1 is connected to one portion of the right ventricle (RV) lead and the negative signal component of C2 is connected to another portion of the right ventricle lead. In this configuration the right ventricle lead would be used to provide the pacing signal.

Accordingly, aspects of the invention involve a DDD device configured to connect a first electrical connection (C1+) to a first output (RV+), a second electrical connection (C2−) to a second output (RV−), and the third (C1−) and fourth (C2+) electrical connections to a third output/reference.

FIG. 6 shows the connection grid 600 being configurable in response to a connection control circuit. The connection grid 600 shown in FIG. 6 is a relatively simple connection grid that allows each terminal to select between the five different outputs. More complex or simple connection grids can also be implemented, including a connection grid that allows for selection applying the pacing control to either or both terminals of the capacitors C1 and C2.

The specific circuit shown in FIG. 6 is merely representative of any number of configurable circuits that can be implemented in accordance with the present invention. For example, the power source for the pacing signals need not be capacitive per se and could be provided by various power providing circuits and electrical elements.

Although not shown, the ventricular sense channel could be implemented using the connections that would remain essentially identical between a conventional DDD device and the embodiments of FIG. 6.

Figure 7:
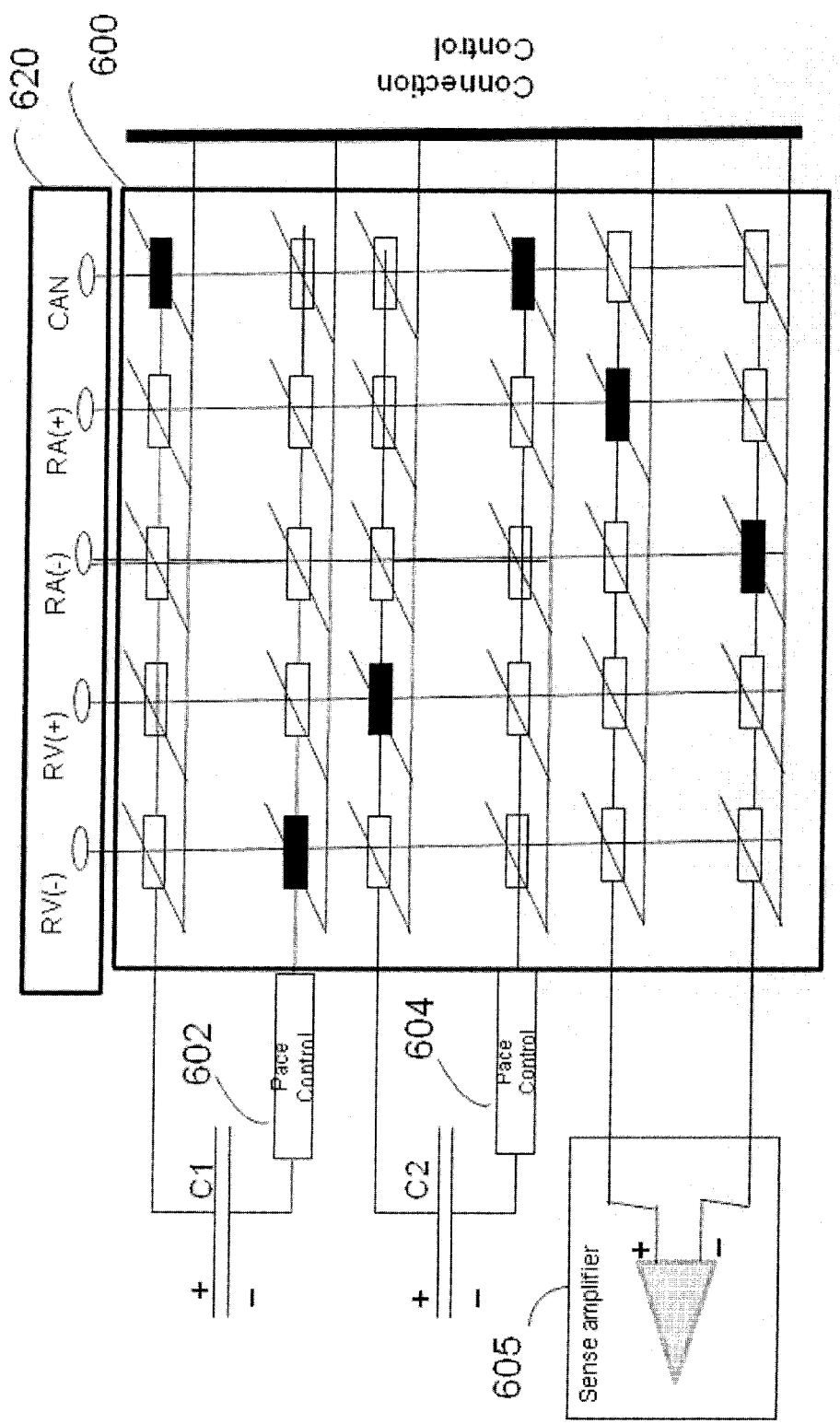
FIG. 7 shows an illustration of a modified DDD device, consistent with an example embodiment of the present invention.

FIG. 7 is similar to FIG. 6, however, the signal polarities have been inverted such that the positive of capacitor C1 and negative of capacitor C2 have been connected to the reference (CAN), while the negative of capacitor C1 is connected to RV(−) and the positive of C2 is connected to RV(+).

Although not shown, the RV sense channel could be implemented in a manner that is similar to those connections in a DDD device.

FIG. 8 shows an illustration a Biventricular DDD CRT device, consistent with an example embodiment of the present invention. FIG. 8 shows three pacing capacitors C1, C2 and C3 that provide pacing output signals for the ventricular channels and the atrial channel respectively. Pace Control 802, 804 and 806 provide various functions for pacing delivery including, but not limited to, timing control, amplitude settings, and pulse duration. The connection grid 800 provides selectable connection between the pacing capacitors C1, C2, C3 and the various outputs 820. The solid boxes of connection grid 800 represent connections between the capacitors C1, C2, C3, and the output directly above. Thus, the negative signal component of C1 and the positive component of C3 are both connected to a reference, such as the can of the CRT device. The positive signal component of C1 is connected to one portion of the right ventricle (RV) lead and the negative signal component of C3 is connected to another portion of the right ventricle lead. In this configuration the right ventricle lead would be used to provide the pacing signal.

Accordingly, aspects of the invention involve a Biventricular CRT device configured to connect a first electrical connection (C1+) to a first output (RV+), a second electrical connection (C3−) to a second output (RV−), and the third (C1−) and fourth (C3+) electrical connections to a third output/reference.

FIG. 8 shows the connection grid 800 being configurable in response to a connection control circuit. The connection grid 800 shown in FIG. 8 is a relatively simple connection grid that allows each terminal to select between the five different outputs. More complex or simple connection grids can also be implemented, including a connection grid that allows for selection applying the pacing control to either or both terminals of the capacitors C1 and C2.

The specific circuit shown in FIG. 8 is merely representative of any number of configurable circuits that can be implemented in accordance with the present invention. For example, the power source for the pacing signals need not be capacitive per se and could be provided by various power providing circuits and electrical elements.

The circuits shown in FIG. 8 used the extra (capacitive) pacing source, previously used for atrial pacing, to configure the RV channel to provide XSTIM dual pulse therapy. This device combines simultaneously biventricular CRT and XSTIM CRT. This can be particularly useful for patients with dilated hearts where the substrate lesion is too large (i.e., due to a major infarct that destroyed the His fibers that activated a region of the LV) for XSTIM to bypass it. Thus, a second LV may be required to synchronize a late activated region in the LV.

Cardiac applications represent a specific embodiment of the invention; however, the present invention is also applicable to other therapies, such as those where high current density spot(s) away from the electrodes are beneficial for stimulating the target including, but not limited to, nerves, muscle, gastric and intestine system, and cortex. For example, U.S. Pat. No. 5,299,569 to Wernicke et al. issued Apr. 5, 1994 (and incorporated herein by reference) describes pacing the vagus nerve to treat a wide variety of disorders. Pacing electrodes are applied directly to the vagus nerve in, for example, the neck. Application of an electrode directly to the vagus nerve creates risk of mechanical injury (e.g., pressure necrosis) to the nerve. Electrodes are placed subcutaneously near (transcutaneously or transvenously coupled) but not on the vagus nerve (VN) in the neck. A reference electrode is placed subcutaneously (transcutaneously or transvenously coupled) on an opposite side of the nerve VN. The electrodes and reference electrode are connected to a pulse generator IPG. With signals as described above, the resulting electrical field captures the vagus nerve. The signals may be selected to have amplitude, frequency and other parameters as more fully described in the '569 patent. It will be appreciated that other alternative examples of using the present invention to pace an organ or the nerve will occur to one of ordinary skill in the art with the benefit of the teachings of the present invention.

The skilled artisan will recognize that the various aspects discussed in connection with the present invention can be implemented in a variety of combinations and manners. Moreover, aspects discussed in connection with the various references disclosed and incorporated herein, including those references indicated at the beginning of this document, can be used in combination with aspects of the present invention. In particular to the extent that the references indicated at the beginning of this document include a number of similar figures and related discussions, the skilled artisan would appreciate the interoperability of aspects disclosed therein even for figures not common between documents. The teachings throughout these documents relate to aspects that can be used in combination with embodiments of the present invention. Accordingly, the documents are incorporated by reference in their entirety. For instance, the U.S. Provisional Patent Application identified by Ser. No. 61/020,511 includes an appendix with figures depicting various pacing electrodes and associated circuitry, and such embodiment(s) can be used in combination with aspects of the present invention.

The various embodiments described above are provided by way of illustration only and should not be construed to limit the invention. Based on the above discussion and illustrations, those skilled in the art will readily recognize that various modifications and changes may be made without strictly following the exemplary embodiments and applications illustrated and described herein. Such modifications and changes do not depart from the true spirit and scope of the present invention.

What is claimed is:

1. A pacing system comprising:
a signal generator that provides a first electrostimulation pulse and a second electrostimulation pulse, each electrostimulation pulse having positive and negative signal components, the first and second pulses including at least partially overlapping opposing polarity waveforms to pace a heart from a single chamber of the heart, the electrostimulation provided for delivery via a pacing lead having a first electrode and a second electrode; and
circuitry for routing at least some of the signal components of the two electrostimulation pulses to the pacing lead by connecting a negative component of a first electrostimulation pulse and a positive component of a second electrostimulation pulse to a common reference and by connecting the positive component of the first electrostimulation pulse to the first electrode and the negative component of the second electrostimulation pulse to the second electrode.

2. The pacing system of claim 1, further including a first capacitive component for providing the first electrostimulation pulse and a second capacitive component for providing the second electrostimulation pulse.

3. The pacing system of claim 1, further including a configurable routing circuit for routing the electrostimulation pulses.

4. The pacing system of claim 1, further including an interface for electrically connecting to two outputs of the signal generator, each output configured for providing a respective one of the first and second electrostimulation pulses, to the pacing lead.

5. The pacing system of claim 1, wherein the signal generator further includes a third electrostimulation output.

6. The pacing system of claim 1, further including a sense input for detecting electrical signals of the heart.

7. The pacing system of claim 1, further including pacing control circuitry for modifying the characteristics of the first and second electrostimulation pulses.

8. The pacing system of claim 1, further including an electrode lead for sensing atrial activity.

9. The pacing system of claim 1, further including the pacing lead, wherein the pacing lead is configured to be disposed in a right ventricle.

10. For use with a cardiac resynchronization therapy (CRT) device designed for biventricular pacing using a first electrostimulation pulse having a positive component provided to a first electrical connection and negative component provided to a second electrical connection and a second electrostimulation pulse with a positive component provided to a third electrical connection and negative component provided to a fourth electrical connection, the first and second pulses including at least partially overlapping opposing polarity waveforms, a circuit comprising:
a first output configured to be connected to a pacing lead;
a second output configured to be connected to the pacing lead;
a third output configured to be connected to a reference point; and
electrical circuitry connecting the first electrical connection to the first output, the fourth electrical connection to the second output, and the second and third electrical connections to the third output.

11. The circuit of claim 10, wherein the electrical circuitry is programmable such that the first and second outputs can be connected to any of the outputs.

12. The circuit of claim 10, wherein each of the two electrostimulation pulses is generated using an independently referenced signal source.

13. The circuit of claim 10, further including two capacitive sources each having respective positive and negative terminals, the positive and negative terminals of the first capacitive source corresponding to the first and second electrical connections, respectively, and the positive and negative terminals of the second capacitive source corresponding to the third and fourth electrical connections, respectively.

14. The circuit of claim 13, wherein each of the two electrostimulation pulses is provided by an independently referenced capacitive source.

15. The circuit of claim 10, further including a sense input for detecting electrical signals of a heart using a pacing lead configured to sense atrial activity.

16. The circuit of claim 10, further including a pacing control circuit for modifying characteristics of the first and second electrostimulation pulses.

17. A device for connecting a pacing lead to a cardiac rhythm therapy (CRT) apparatus designed for dual chamber pacing using two electrostimulation pulses each having positive and negative signal components, the first electrostimulation pulse having a positive component provided to a first output and a negative component provided to a second output, the second electrostimulation pulse having a positive component provided to a third output and a negative component provided to a fourth output, wherein the pulses include at least partially overlapping opposing polarity waveforms, and wherein, for dual chamber pacing, the first and second outputs are for use with a first pacing lead and the third and fourth outputs are for use by a second pacing lead, the device comprising:
    a connector housing for physically mating with
        two interfaces of the CRT apparatus, the first interface providing the first and second signal components and the second interface providing the third and fourth signal components, each interface arranged for physically mating with a pacing lead, and
        a single pacing lead; and
    electrical connections from the second and third outputs to a common reference point and from the first and fourth outputs to respective inputs of the single pacing lead, thereby allowing single chamber pacing using the single pacing lead.

18. The device of claim 17, wherein the connector housing is further configured for physically mating with a third interface of the CRT apparatus.

19. The device of claim 18, wherein the electrical connections further include a connection between a sense signal of the third interface and the single pacing lead.

20. The device of claim 18, wherein the electrical connections further include connections between fifth and sixth outputs and a second pacing lead.

\* \* \* \* \*